(12) United States Patent
Sonoda et al.

(10) Patent No.: US 9,365,927 B2
(45) Date of Patent: Jun. 14, 2016

(54) DEPOSITION METHOD AND COLLECTION METHOD

(71) Applicant: Sharp Kabushiki Kaisha, Osaka (JP)

(72) Inventors: Tohru Sonoda, Osaka (JP); Shinichi Kawato, Osaka (JP); Satoshi Inoue, Osaka (JP); Satoshi Hashimoto, Osaka (JP)

(73) Assignee: Sharp Kabushiki Kaisha, Osaka (JP)

( * ) Notice: Subject to any disclaimer, the term of this patent is extended or adjusted under 35 U.S.C. 154(b) by 119 days.

(21) Appl. No.: 14/298,844

(22) Filed: Jun. 6, 2014

(65) Prior Publication Data

US 2014/0299058 A1    Oct. 9, 2014

Related U.S. Application Data

(62) Division of application No. 13/976,443, filed as application No. PCT/JP2011/079445 on Dec. 20, 2011, now abandoned.

(30) Foreign Application Priority Data

Dec. 27, 2010   (JP) .................................. 2010-291199

(51) Int. Cl.
*C23C 16/04* (2006.01)
*C23C 16/44* (2006.01)
(Continued)

(52) U.S. Cl.
CPC ............ *C23C 16/4401* (2013.01); *C12M 33/00* (2013.01); *C23C 14/564* (2013.01); *H01L 31/186* (2013.01); *H01L 51/0011* (2013.01)

(58) Field of Classification Search
CPC ...... C23C 14/04; C23C 14/042; C23C 14/24; C23C 14/243; C23C 16/04; C23C 16/042; C23C 16/4401; C23C 16/4404; C23C 16/4485
See application file for complete search history.

(56) References Cited

U.S. PATENT DOCUMENTS 5,366,764 A * 11/1994 Sunthankar ............. C23C 14/22
427/248.1
5,472,509 A   12/1995 Hiroshi
(Continued)

FOREIGN PATENT DOCUMENTS

JP     4-236759 A     8/1992
JP     5-247628 A     9/1993
(Continued)

OTHER PUBLICATIONS

Restriction Requirement for U.S. Appl. No. 13/976,443 in the name of Tohru Sonoda et al. Notification Date: Oct. 11, 2013.
(Continued)

*Primary Examiner* — Bret Chen
(74) *Attorney, Agent, or Firm* — Morrison & Foerster LLP

(57) ABSTRACT

Techniques for producing an organic electroluminescent element while collecting a vapor deposition material that is vapor-deposited on a vapor deposition device, collecting a vapor-deposited film by use of a collection device, and producing an organic electroluminescent element by use of a collection device. In one example, a film is provided on at least a part of a surface of each of a vapor deposition preventing plate and a shutter of a vacuum chamber on which surface vapor deposition particles are vapor-deposited, the film being provided so as to be peeled off from the each of the vapor deposition preventing plate and the shutter, and the film being made of a material differing in at least one of a melting point, a sublimation point, solubility in a given solvent, microbial biodegradability, and photodegradability from a material of which a vapor-deposited film that is formed on the film is made.

9 Claims, 10 Drawing Sheets

(51) Int. Cl.
*C23C 14/56* (2006.01)
*H01L 31/18* (2006.01)
*C12M 1/26* (2006.01)
*H01L 51/00* (2006.01)

(56) References Cited

U.S. PATENT DOCUMENTS

| | | |
|---|---|---|
| 5,585,272 A | 12/1996 | Pierce et al. |
| 5,641,679 A | 6/1997 | Pierce |
| 5,688,685 A | 11/1997 | Pierce |
| 5,773,283 A | 6/1998 | Pierce |
| 5,834,582 A | 11/1998 | Sinclair et al. |
| 6,179,923 B1 * | 1/2001 | Yamamoto .............. C23C 14/12 118/719 |
| 7,914,620 B2 * | 3/2011 | Chi ....................... C23C 14/564 118/724 |
| 2007/0148337 A1 | 6/2007 | Nichols et al. |
| 2008/0115729 A1 * | 5/2008 | Oda ..................... C23C 14/243 118/726 |
| 2009/0229524 A1 | 9/2009 | Kim et al. |
| 2010/0248416 A1 | 9/2010 | Priddy et al. |
| 2010/0297349 A1 | 11/2010 | Lee et al. |
| 2011/0036267 A1 | 2/2011 | Kadowaki et al. |
| 2011/0041760 A1 | 2/2011 | Kadowaki et al. |
| 2011/0041761 A1 | 2/2011 | Kadowaki et al. |
| 2011/0041763 A1 | 2/2011 | Kadowaki et al. |
| 2011/0048320 A1 | 3/2011 | Choi et al. |
| 2011/0165320 A1 | 7/2011 | Choi et al. |
| 2012/0202058 A1 * | 8/2012 | Takahira ............ C08G 18/4202 428/355 EN |
| 2013/0236723 A1 | 9/2013 | Ishiguro et al. |

FOREIGN PATENT DOCUMENTS

| | | | |
|---|---|---|---|
| JP | 7-289240 | * | 11/1995 |
| JP | 8-41624 A | | 2/1996 |
| JP | 10-168559 A | | 6/1998 |
| JP | 10-286566 | * | 10/1998 |
| JP | 2002-190389 A | | 7/2002 |
| JP | 2002-292346 A | | 10/2002 |
| JP | 2005-149924 A | | 6/2005 |
| JP | 2008-88465 A | | 4/2008 |
| JP | 2008-127642 A | | 6/2008 |
| JP | 2008-223102 A | | 9/2008 |
| JP | 2009-521714 A | | 6/2009 |
| JP | 2010-270396 A | | 12/2010 |
| WO | WO-2009/133836 A1 | | 11/2009 |
| WO | WO-2009/133837 A1 | | 11/2009 |
| WO | WO-2009/133838 A1 | | 11/2009 |
| WO | WO-2009/133839 A1 | | 11/2009 |

OTHER PUBLICATIONS

Non-Final Office Action for U.S. Appl. No. 13/976,443 in the name of Tohru Sonoda et al. Notification Date: Dec. 16, 2013.
Final Office Action for U.S. Appl. No. 13/976,443 in the name of Tohru Sonoda et al. Notification Date: Mar. 7, 2014.
International Search Report received for PCT Patent Application No. PCT/JP2011/079445, mailed on Mar. 6, 2012, 8 pages (4 pages of English Translation and 4 pages of ISR).
International Preliminary Report on Patentability received for PCT Patent Application No. PCT/JP2011/079445, mailed Jul. 2, 2013 (11 pages of English Translation and 7 pages of IPRP).
Non-Final Office Action for U.S. Appl. No. 14/091,187. Notification date: May 16, 2014.
Final Office Action for U.S. Appl. No. 14/091,187. Mail Date: Aug. 28, 2014. 14 pages.
Advisory Action for U.S. Appl. No. 14/091,187. Notification Date: Nov. 18, 2014. 5 pages.
Non-Final Office Action for U.S. Appl. No. 14/091,187. Notification date: Feb. 4, 2015. 17 pages.
Final Office Action for U.S. Appl. No. 14/091,187. Notification date: May 14, 2015. 16 pages.

* cited by examiner

DEPOSITION METHOD AND COLLECTION METHOD

CROSS REFERENCE TO RELATED APPLICATIONS

This application is a Continuation of U.S. patent application Ser. No. 13/976,443, filed Dec. 20, 2011, which is a U.S. National Phase patent application of PCT/JP2011/079445, filed Dec. 20, 2011, which claims priority to Japanese patent application no. 2010-291199, filed Dec. 27, 2010, each of which is hereby incorporated by reference in the present disclosure in its entirety.

TECHNICAL FIELD

The present invention relates to a vapor deposition device and a collection device for collecting vapor deposition materials that are vapor-deposited on an unnecessary part.

BACKGROUND ART

Recent years have witnessed practical use of a flat-panel display in various products and fields. This has led to a demand for a flat-panel display that is larger in size, achieves higher image quality, and consumes less power.

Under such circumstances, great attention has been drawn to an organic EL display device that (i) includes an organic electroluminescence (hereinafter abbreviated to "EL") element which uses EL of an organic material and that (ii) is an all-solid-state flat-panel display which is excellent in, for example, low-voltage driving, high-speed response, self-emitting, and wide viewing angle characteristics.

An organic EL display device includes, for example, (i) a substrate made up of members such as a glass substrate and TFTs (thin film transistors) provided to the glass substrate and (ii) organic EL elements provided on the substrate and connected to the TFTs.

An organic EL element is a light-emitting element capable of emitting high-luminance light by low-voltage direct-current drive. The organic EL element has a structure in which a first electrode, an organic EL layer, and a second electrode are stacked in this order, and the first electrode is electrically connected to the TFT.

As the organic EL layer, an organic layer having a structure in which a hole injection layer, a hole transfer layer, an electron blocking layer, a luminescent layer, a hole blocking layer, an electron transfer layer, an electron injection layer, and the like are stacked together is provided between the first electrode and the second electrode.

For example, a full-color organic EL display device typically includes, as sub-pixels aligned on a substrate, organic EL elements of red (R), green (G), and blue (B). The full-color organic EL display device carries out an image display by, with use of TFTs, selectively causing the organic EL elements to each emit light with a desired luminance.

In production of such an organic EL display device, a luminescent layer of a predetermined pattern made of an organic light-emitting material which emits light of the colors is formed for each organic EL element serving as a light-emitting element.

The organic EL layer and the second electrode can be prepared by, for example, (i) a vacuum vapor deposition method which uses a vapor deposition mask referred to as a shadow mask, (ii) an inkjet method, and (iii) a laser transfer method.

Among the methods listed above, the vacuum vapor deposition method is most typically used. According to the vacuum vapor deposition method, a vapor deposition material contained in a heating container called a crucible or a boat, is heated in a highly vacuum so as to be sublimated, and then a thin film made of the vapor deposition material is deposited on a substrate.

In this case, it is possible to form a vapor-deposited film only in a desired region of the substrate by (i) fixing a shadow mask in close contact with the substrate, the shadow mask being open in the desired region and (ii) vapor-depositing the vapor deposition material on the substrate via an opening of the shadow mask.

However, the vacuum vapor deposition method causes a loss of all the vapor deposition material except the vapor deposition material of which the vapor-deposited film deposited on the substrate is made. Therefore, the vapor deposition material except the vapor deposition material of which the vapor-deposited film deposited on the substrate is made is not made into a vapor-deposited film to be provided in an organic EL display device.

In other words, the vapor deposition material is all wasted which adheres to, for example, (i) a shutter which determines whether or not vapor deposition particles are emitted toward the substrate which is provided directly above, for example, the crucible containing the vapor deposition material, (ii) a vapor deposition preventing plate which is provided in a replaceable state so that an inside of a chamber of a vapor deposition device is not contaminated with the vapor deposition material, and (iii) a non-opening of the shadow mask.

The second electrode is typically made of metal, which is lower in unit material cost as compared to an organic material of which the organic EL layer is made. Meanwhile, the organic material of which the organic EL layer is made is a special functional material that possesses properties such as electroconductivity, a carrier transferring property, a light-emitting property, and thermal and electrical stability, and the organic material is extremely high in unit material cost.

Despite the above fact, all the vapor deposition material except the vapor deposition material of which the vapor-deposited film deposited on the substrate is made is lost (described earlier). This causes an increase in the amount of use of a material per substrate to be subjected to a vapor deposition process, so that a cost for the vapor deposition process is high, and consequently the organic EL display device increases in cost.

A method for solving such a problem may be exemplified by a method for collecting and reusing materials adherent to a part other than a substrate.

For example, Patent Literature 1 discloses a water jet device which causes water jet spraying to collect an adherent film adherent to a film formation jig.

FIG. 15 is a view schematically illustrating a configuration of the water jet device disclosed in Patent Literature 1.

The water jet device illustrated in FIG. 15 includes a table 126 which is a working table for carrying out a cleaning operation and a working chamber 122 which is box-shaped so as to cover the table 126 from above. The working chamber 122 has, on its side surfaces, doors via which a film formation jig 125 that is an object to be cleaned is carried in/out onto/from the table 126.

The working chamber 122 can be hermetically sealed so that during the cleaning operation, splashes of water jet can be prevented from leaking out of the working chamber 122.

The working chamber 122 includes a robot 121 which has a tip capable of three-dimensionally moving in accordance with a shape of a surface of the film formation jig 125 on which surface an adherent film is formed, the film formation jig 125 being an object to be cleaned (a cleaning target).

The robot 121 has an arm whose tip is provided with a cleaning gun 151. A high-pressure water generating device 152 for generating high-pressure water is provided outside and in proximity to the working chamber 122 so as to supply high-pressure water to the cleaning gun 151 via the robot 121.

Note that a pure water producing device 151 supplies, to the high-pressure water generating device 152, city water from which ions have been removed.

The working chamber 122 further includes a sprayer 159 for moistening an inner wall of the working chamber 122 and (ii) an exhaust fan 162 for setting a pressure inside the working chamber 122 to be negative.

The table 126 has many holes provided in a net-like pattern, and a centrifugal separator 157 is provided under the table 126. The centrifugal separator 157 includes a fixed container 154 and a rotating container 156. The rotating container 156 coaxially rotates at a high speed in the fixed container 154 whose skin has many holes and whose inner surface has a filtering member 155 which is provided so as to cover the many holes.

In a case where the cleaning gun 151 sprays water jet at a water pressure of 30 MPa to 200 MPa over the adherent film of the film formation jig 125 which is placed on a cleaning jig platen 153 provided on the table 126 of the working chamber 122, high-pressure water sprayed over the film formation jig 125 becomes suspended water containing adherent film pieces from the adherent film of the film formation jig 125.

Then, the suspended water, together with water burst from the sprayer 159, flows, directly or along an inner wall surface of the working chamber 122, downward via the many holes of the table 126, and then enters the rotating container 156, where the suspended water and the water burst from the sprayer 159 are subjected to centrifugation by the centrifugal separator 157, so as to be separated into adherent film pieces and wastewater. The adherent film can thus be collected.

Note that the wastewater from a drain 158 returns to the high-pressure water generating device 152 via a pipe 177.

Patent Literature 1 discloses that according to the water jet device, it is possible to collect and reuse the attached film of the film formation jig 125 while the film formation jig 125 is ground in a small amount and waste is generated in a reduced amount.

CITATION LIST

Patent Literature

Patent Literature 1
Japanese Patent Application Publication, Tokukai, No. 2002-292346 A (Publication Date: Oct. 8, 2002)

SUMMARY OF INVENTION

Technical Problem

The following description will discuss, with reference to FIG. 14, a problem of a conventional vacuum vapor deposition device 21 which is used for formation of an organic EL layer during a process for producing an organic EL display device.

FIG. 14 is a view schematically illustrating a configuration of the conventional vacuum vapor deposition device 21.

A vacuum chamber 5 includes a vapor deposition source(s) 2, vapor deposition preventing plates 3, and a shutter 4.

The number of the vapor deposition source(s) 2 provided in the vacuum chamber 5 is one (1). The vapor deposition preventing plates 3 prevent other components of the vacuum chamber 5 from being contaminated with vapor deposition particles.

The shutter 4 prevents the vapor deposition particles from being released (spouted) into the vacuum chamber 5 when vapor deposition does not need to be carried out (e.g. during a time period before vapor deposition is carried out at a stable speed, while a substrate 101 is absent, or during a time period in which the substrate 101 and a shadow mask 110 are positioned so as to be adhered to each other). In other words, the shutter 4 has a function of covering/uncovering release holes 6 of the respective vapor deposition preventing plates 3.

Note that a vapor deposition material released from the vapor deposition source 2 is adhering to the vapor deposition preventing plates 3, the shutter 4, and the like while a vapor deposition process is being carried out. When the vapor deposition material adheres to the vapor deposition preventing plates 3, the shutter 4, and the like in a certain amount or more, the vapor deposition material peels off due to, for example, its own weight and then contaminates an inside of the chamber 5. Hence, it is necessary to replace the vapor deposition preventing plates 3, the shutter 4, and the like with new ones on a regular basis.

According to the conventional vacuum vapor deposition device 21 thus configured, all the vapor deposition material except the vapor deposition particles reaching the substrate 101 is lost. The adherent film adherent to a place other than the substrate 101 is not efficiently collected and reused for the following reasons.

A vapor deposition preventing plate, a shutter, and the like provided in a vacuum vapor deposition device are specially designed or designed to be specially-shaped in accordance with a shape of the vacuum vapor deposition device.

Hence, there has been no versatile method that is applicable to any vapor deposition preventing plate and any shutter and that makes it possible to efficiently collect and reuse adherent films adherent to the vapor deposition preventing plate and the shutter.

Therefore, there have merely been (i) a method in which a vapor deposition preventing plate, a shutter, and the like are removed from a vacuum vapor deposition device, and then adherent films adherent to the vapor deposition preventing plate, the shutter, and the like are scraped off surfaces of the vapor deposition preventing plate, the shutter, and the like on which surfaces the adherent films adhere, or purified by separation with use of a sublimation and purification device which is provided separately from the vacuum vapor deposition device, (ii) a method in which a vapor deposition preventing plate, a shutter, and the like are removed from a vacuum vapor deposition device, and then adherent films adherent to the vapor deposition preventing plate, the shutter, and the like are collected with use of the water jet device disclosed in Patent Literature 1, and (iii) the like.

According to the methods, it is necessary to remove a vapor deposition preventing plate, a shutter, and the like from a vacuum vapor deposition device and then to replace the vapor deposition preventing plate, the shutter, and the like with new ones. The removal and replacement of the vapor deposition preventing plate, the shutter, and the like requires much time, and vapor deposition cannot be carried out during the removal and replacement. This results in a decrease in productivity (throughput) of the vacuum vapor deposition device.

Further, in a case where adherent films adherent on surfaces of the vapor deposition preventing plate, the shutter, and the like are scraped off the surfaces of the vapor deposition preventing plate, the shutter, and the like on which surfaces the adherent films adhere, or the adherent films are directly sprayed with water jet, the vapor deposition preventing plate, the shutter, and the like are damaged, so that inclusion of impurities in the vapor deposition preventing plate, the shutter, and the like is highly likely to occur.

According to the methods, it is also necessary to provide a relatively expensive collection device separately from a vacuum vapor deposition device. Therefore, reuse of an expensive material eventually costs high. This reduces an effect of a reduction in cost.

Meanwhile, use of the water jet device disclosed in Patent Literature 1 as a collection device causes the following problem.

Since, it is necessary to directly spray water jet over the adherent film adherent to the film formation jig 125, it is difficult to process adherent films while film formation jigs 125 are being stacked. This causes a problem such that fewer adherent films are processed at one time.

Furthermore, in a case where the film formation jig 125 is large in size, the water jet device accordingly becomes large in size. This results in an increase in device cost.

The present invention has been made in view of the problems, and an object of the present invention is to provide (i) a vapor deposition device which is highly productive and is capable of collecting a vapor deposition material with no increase in device price and (ii) a collection device which is capable of causing inclusion of impurities to be less likely to occur and collecting the vapor deposition material with high efficiency and at low cost.

Solution to Problem

In order to attain the object, a vapor deposition device of the present invention includes: a vapor deposition chamber in which vapor deposition particles released from a vapor deposition source are vapor-deposited on a substrate, the vapor deposition particles being vapor-deposited on the substrate when released from the vapor deposition source in a first direction during a first period, the vapor deposition particles being vapor-deposited on a vapor deposition preventing member when released from the vapor deposition source in a second direction, which is different from the first direction, during the first period, or released from the vapor deposition source during a second period, which is different from the first period, the vapor deposition preventing member being removable from the vapor deposition device, a film being provided on at least a part of a surface of the vapor deposition preventing member on which surface the vapor deposition particles are vapor-deposited, the film being provided so as to be peeled off from the vapor deposition preventing member, and the film being made of a material differing in at least one of a melting point, a sublimation point, solubility in a given solvent, microbial biodegradability, and photodegradability from a material of which a vapor-deposited film that is formed on the film is made.

According to the configuration, a film is provided on at least a part of a surface of the vapor deposition preventing member on which surface the vapor deposition particles are vapor-deposited, the film being provided so as to be peeled off from the vapor deposition preventing member. This causes the vapor deposition particles to be vapor-deposited not on the vapor deposition preventing member but on the film.

Since the film on which the vapor deposition particles are vapor-deposited can be easily peeled off from the vapor deposition preventing member, it is possible to replace the film with a new one in a relatively short time.

Meanwhile, according to a conventional vapor deposition device including no film, it is necessary to remove a vapor deposition preventing member from a vacuum vapor deposition device and then to replace the vapor deposition preventing member with a new one. The removal and replacement of the vapor deposition member requires much time, and vapor deposition cannot be carried out during the removal and replacement. This results in a decrease in productivity (throughput) of the vacuum vapor deposition device.

Further, it is possible to increase productivity of the vapor deposition device only by providing the film.

Since the film is made of a material differing in at least one of a melting point, a sublimation point, solubility in a given solvent, microbial biodegradability, and photodegradability from a material of which a vapor-deposited film that is formed on the film is made, it is possible to separate, with relative ease and no fear of inclusion of impurities, the film and the vapor-deposited film that is formed on the film.

With the configuration, therefore, it is possible to provide a vapor deposition device which is highly productive and is capable of collecting a vapor deposition material with no increase in device price.

In order to attain the object, a collection device of the present invention includes: a film which is provided in a vapor deposition device mentioned above and on which a vapor-deposited film is formed; and a separating section for separating the vapor-deposited film from the film on which the vapor-deposited film is formed.

According to the configuration, the film and the vapor-deposited film that is formed on the film is separated by the separating section by use of a difference between the film and the vapor-deposited film that is formed on the film in at least one of a melting point, a sublimation point, solubility in a given solvent, microbial biodegradability and photodegradability. Therefore, unlike a conventional method, it is possible to reduce the possibility that, in a case where a vapor-deposited film is scraped off a surface of a vapor deposition preventing member on which surface the vapor-deposited film is vapor-deposited, or the vapor-deposited film vapor-deposited on the vapor deposition preventing member is directly sprayed with water jet, the vapor deposition preventing member is damaged and causes inclusion of impurities in the vapor deposition preventing member.

Therefore, it is possible to provide a collection device which is capable of causing inclusion of impurities to be less likely to occur and collecting the vapor deposition material with high efficiency and at low cost.

Advantageous Effects of Invention

The vapor deposition device of the present invention is configured such that the vapor deposition particles are vapor-deposited on the substrate when released from the vapor deposition source in a first direction during a first period, the vapor deposition particles are vapor-deposited on a vapor deposition preventing member when released from the vapor deposition source in a second direction, which is different from the first direction, during the first period, or released from the vapor deposition source during a second period, which is different from the first period, the vapor deposition preventing member being removable from the vapor deposition device, a film is provided on at least a part of a surface of the vapor deposition preventing member on which surface the vapor deposition particles are vapor-deposited, the film being provided so as to be peeled off from the vapor deposition preventing member, and the film is made of a material differing in at least one of a melting point, a sublimation point, solubility in a given solvent, microbial biodegradability, and photodegradability from a material of which a vapor-deposited film that is formed on the film is made.

The collection device of the present invention thus includes: a film which is provided in a vapor deposition device mentioned above and on which a vapor-deposited film is formed; and a separating section for separating the vapor-deposited film from the film on which the vapor-deposited film is formed.

Hence, it is possible to realize (i) a vapor deposition device which is highly productive and is capable of collecting a vapor deposition material with no increase in device price and (ii) a collection device which is capable of causing inclusion of impurities to be less likely to occur and collecting the vapor deposition material with high efficiency and at low cost.

DESCRIPTION OF EMBODIMENTS

Embodiments of the present invention will be described below in detail with reference to the drawings. Note, however, that the dimensions, materials, shapes, relative locations, and the like of respective constituent elements described in Embodiments are illustrative only, and that the scope of the present invention should not be narrowly construed based on them.

Note that, each of the following Embodiments will deal with a deposition device and a collection device each used for a process for producing an organic EL display device as an example of a vapor deposition device and a collection device of the present invention. Embodiments are, however, not limited to this. The vapor deposition device and the collection device of the present invention can be used in production processes carried out in various fields.

[Embodiment 1]

Figure 11:
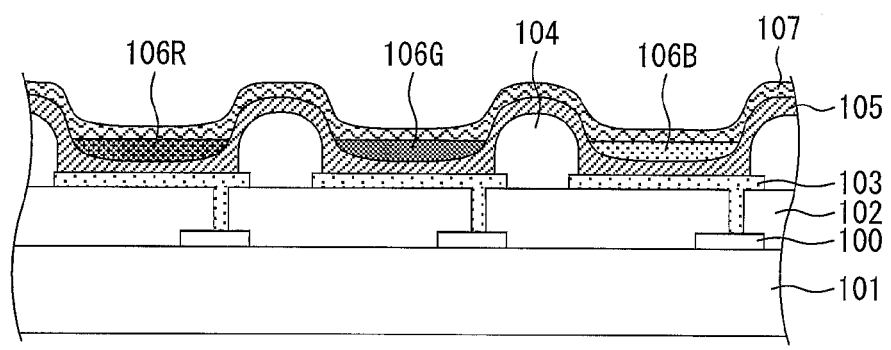
FIG. 11 is a cross-sectional view of organic EL elements constituting a display section of an organic EL display device.

FIG. 11 is a cross-sectional view of organic EL elements constituting a display section of an organic EL display device.

There are provided, on a substrate 101 where thin film transistors (TFTs) are provided, an interlayer insulating film 102, first electrodes 103, and edge covers 104.

For example, alkali-free glass or plastic can be employed as the substrate 101. Embodiment 1 employs, as the substrate 101, an alkali-free glass substrate having a thickness of 0.7 mm.

A known photosensitive resin can be employed as each of the interlayer insulating film 102 and the edge covers 104. Examples of such a known photosensitive resin encompass an acrylic resin and a polyimide resin.

In Embodiment 1, a photosensitive acrylic resin is employed as each of the interlayer insulating film 102 and the edge covers 104.

The first electrodes 103 are formed by (i) depositing an electrode material by a method such as sputtering and (ii) then patterning the electrode material in shapes for respective pixels by photolithography and etching.

The first electrodes 103 can be made of any of various electrically conductive materials. Note, however, that the first electrodes 103 need to be transparent or semi-transparent in a case where the organic EL display device is a bottom emission organic EL element in which light is emitted towards a substrate side. Meanwhile, a second electrode 107 needs to be transparent or semi-transparent in a case where the organic EL display device is a top emission organic EL element in which light is emitted from a surface opposite to the substrate side.

The TFTs are prepared by use of a known method. Note that Embodiment 1 will discuss how to produce an active matrix organic EL display device in which the TFTs are provided for respective pixels. Note, however, that Embodiment 1 is not limited to this. Embodiment 1 is applicable also to a passive matrix organic EL display device in which no TFT is provided.

The edge covers 104 cover edge parts of the first electrodes 103 so as to prevent the corresponding first electrodes 103 and the second electrode 107 from short-circuiting due to a reduction in thickness of an organic EL layer and/or concentration of electric fields in the edge parts of the first electrodes 103. Each first electrode 103 is exposed in a corresponding area between adjacent edge covers 104. Note that such a corresponding area serves as a light-emitting section of a corresponding pixel.

Each organic EL layer is formed on a corresponding first electrode 103. The organic EL layer is made up of, for example, a hole injection layer/hole transfer layer 105, a luminescent layers (106R, 106G, and 106B), and an electron transfer layer/an electron injection layer (not illustrated).

The organic EL layer can, as needed, further include a carrier blocking layer (not illustrated) for blocking a flow of carriers such as holes and electrons. A single layer can have a plurality of functions. For example, the hole injection layer/hole transfer layer 105 can serve as both a hole injection layer and a hole transfer layer.

In Embodiment 1, (a) the first electrodes 103, serving as an anode, (b) the hole injection layer-/hole transfer layer 105, (c) the luminescent layers (106R, 106G, and 106B), (d) the electron injection layer (not illustrated), (e) the electron transfer layer (not illustrated), and (f) the second electrode 107 serving as a cathode, are stacked in this order from a first electrode 103 side.

Note that, in a case where the first electrode 103 is intended to serve as a cathode, the order in which the layers are stacked is reversed.

Embodiment 1 employs a bottom emission organic EL element, and ITO (indium tin oxide) is employed as the first electrode 103. Note that the organic EL layer can be made of a known material.

Each of the luminescent layers (106R, 106G, and 106B) can be made of a single material or made of a host material mixed with another material as a guest material or a dopant. In Embodiment 1, each of the luminescent layers (106R, 106G, and 106B) is made of a single material.

Figure 12:
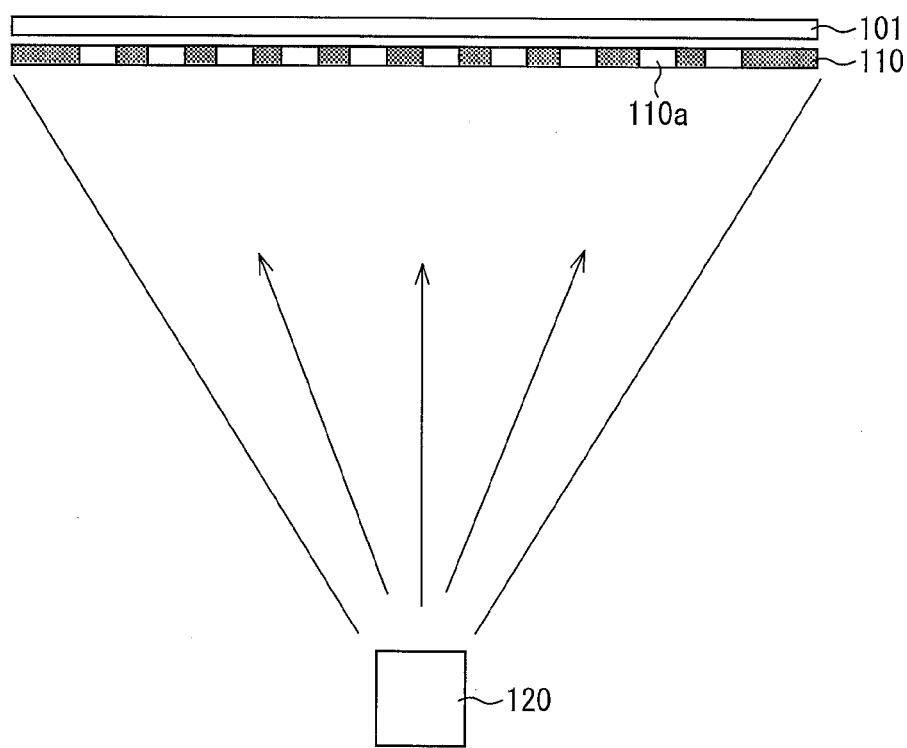
FIG. 12 is a schematic view of a method for forming a patterned vapor-deposited film on a substrate by use of a vacuum vapor deposition.
Figure 13:
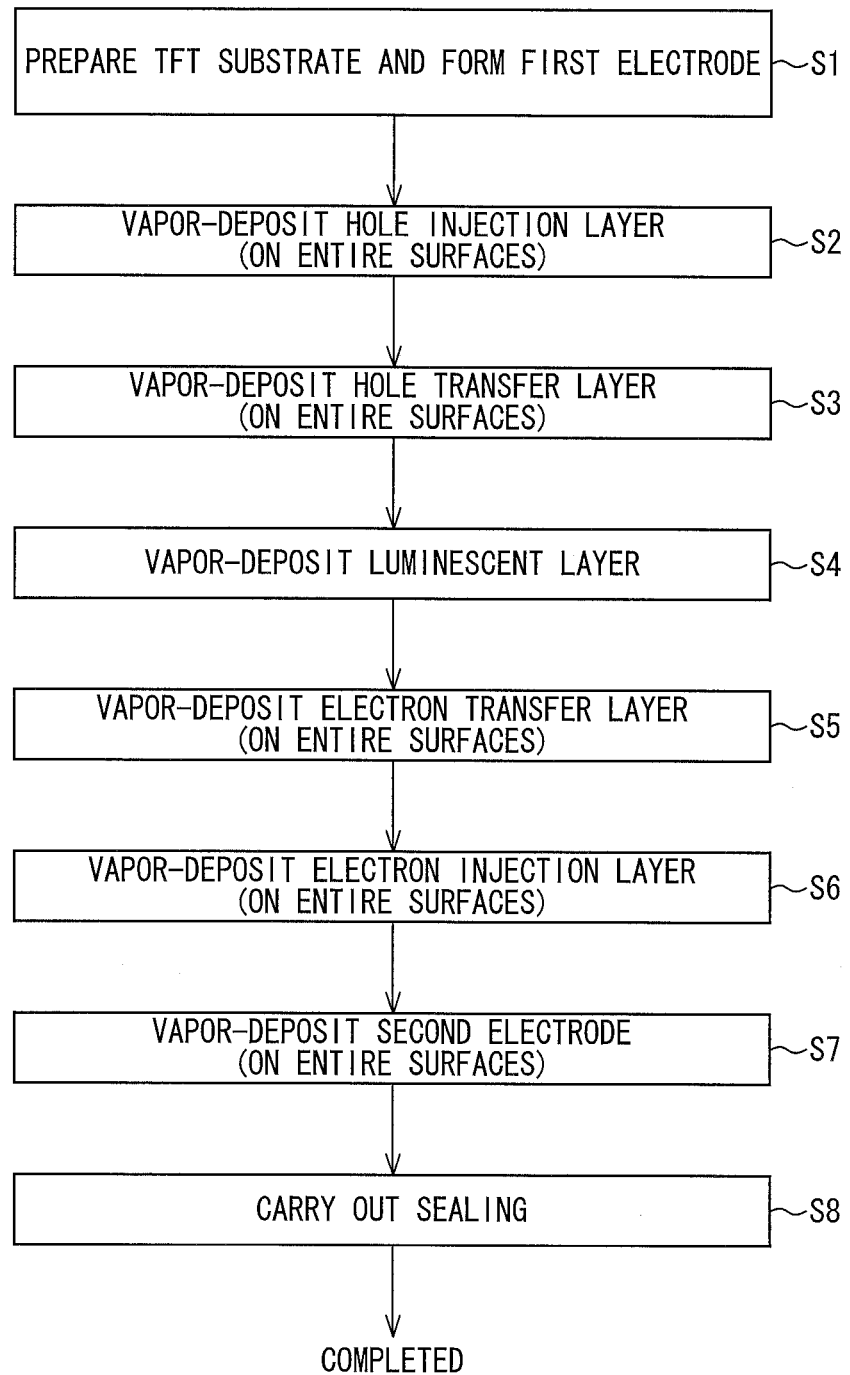
FIG. 13 is a view illustrating a process for producing an organic EL display device.

The following description will discuss, with reference to FIGS. 12 and 13, a method for forming the organic EL layers on the substrate 101 on which none of the organic EL layers illustrated in FIG. 11 have been formed.

FIG. 12 is a schematic view of a method for forming a patterned vapor-deposited film on a substrate by use of a vacuum vapor deposition.

As illustrated in FIG. 12, a vapor deposition material is heated and sublimated by a vapor deposition source 120. Vapor deposition particles obtained by sublimating the vapor deposition material pass through a shadow mask 110 having openings 110a in respective desired positions thereof, and then reach the substrate 101 on which none of the organic EL layers illustrated in FIG. 11 have been formed.

The shadow mask 110 adheres to the substrate 101. This allows a vapor-deposited film to be formed in a desired position of the substrate 101.

In the case of FIG. 11 in which the hole injection layer/hole transfer layer 105, the electron transfer layer (not illustrated), the electron injection layer (not illustrated), and the second electrode 107 are stacked, film formation is carried out with respect to the entire display section. Therefore, film formation is carried out by using, as the shadow mask 110, an open mask which is open in the entire display section and only in a region in which the film formation needs to be carried out.

Meanwhile, in a case where film formation is carried out with respect to the luminescent layers (106R, 106G, and 106B) in FIG. 11, the film formation is carried out by use of a fine mask which is open only in a place in which the film formation is carried out (e.g., for each sub-pixel).

FIG. 13 illustrates a process for producing an organic EL display device.

First, the substrate 101 obtained by forming the first electrodes 103 on a TFT substrate is formed is formed (S1).

Then, the hole injection layer/hole transfer layer 105 is formed on the entire substrate 101 by use of a vacuum vapor deposition method (S2 and S3).

Subsequently, the luminescent layers (106R, 106G, and 106B) are formed in respective given places by the vacuum vapor deposition method with use of a fine mask as the shadow mask 110 (S4).

Thereafter, the electron transfer layer, the electron injection layer, and the second electrode 107 are formed in this order by the vacuum vapor deposition method (S5, S6, and S7).

Note that the second electrode 107 can be formed by a method other than the vacuum vapor deposition method such as a sputtering method.

In order to prevent a deterioration of the organic EL elements due to moisture and/or oxygen in the air, sealing of a region in which the organic EL elements are provided (the display section) is carried out with respect to the substrate thus subjected to vapor deposition (S8).

The sealing may be carried out by, for example, a method in which a film which is difficult to transmit by moisture and/or oxygen is formed by, for example, a CVD method, or a method in which glass substrates, for example are combined together with use of, for example, an adhesive.

The organic EL display device, which is prepared by the above process, can carry out a desired display by supplying, from a drive circuit provided outside the organic EL display device, electric currents to the organic EL elements provided for the respective pixels.

Figure 1:
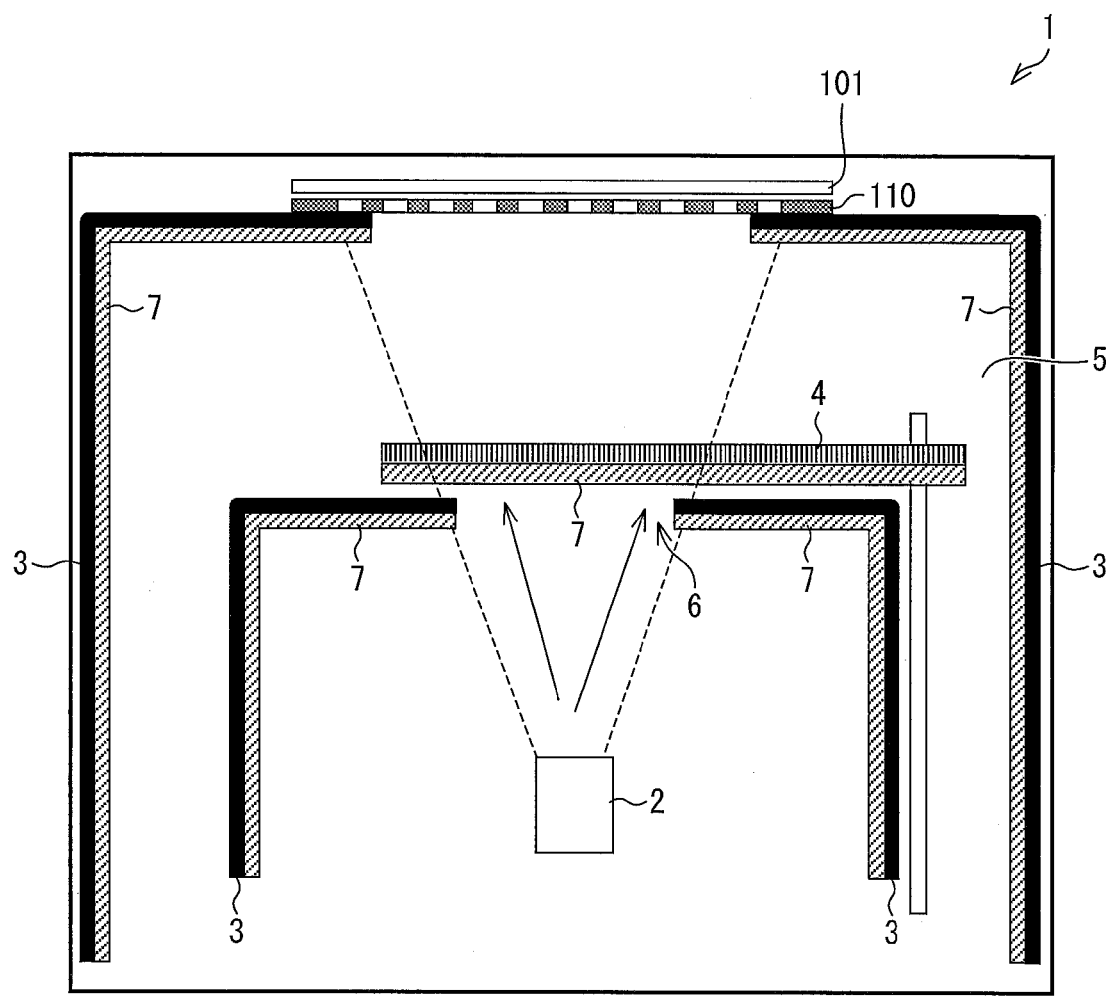
FIG. 1 is a view schematically illustrating a configuration of the vacuum vapor deposition device according to Embodiment 1 of the present invention.

The following description will discuss, with reference to FIG. 1, a vacuum vapor deposition device 1 to be used for forming, during the process for producing the organic EL display device illustrated in FIG. 13, the organic EL layers on the substrate 101 obtained by forming the first electrodes 103 on the TFT substrate.

FIG. 1 is a view schematically illustrating a configuration of the vacuum vapor deposition device 1.

A vacuum chamber 5 (vapor deposition room) includes a vapor deposition source(s) 2, vapor deposition preventing plates 3 (vapor deposition preventing member), and a shutter 4 (vapor deposition preventing member).

The number of the vapor deposition source(s) 2 provided in the vacuum chamber 5 is one (1). The vapor deposition preventing plates 3 prevent other components of the vacuum chamber 5 from being contaminated with vapor deposition particles.

The shutter 4 prevents the vapor deposition particles from being released (spouted) into the vacuum chamber 5 when vapor deposition does not need to be carried out (e.g. during a time period before vapor deposition is carried out at a stable speed, while a substrate 101 is absent, or during a time period in which the substrate 101 and a shadow mask 110 are positioned so as to be adhered to each other). In other words, the shutter 4 has a function of covering/uncovering release holes 6 of the respective vapor deposition preventing plates 3.

As illustrated in FIG. 1, films 7, which can be peeled off from the vapor deposition preventing plates 3 and the shutter 4, are provided on surfaces of the vapor deposition preventing plates 3 and the shutter 4 on which surfaces the vapor deposition particles are vapor-deposited.

According to Embodiment 1, the films 7 are provided on the entire surfaces of the vapor deposition preventing plates 3 and the shutter 4 on which surfaces the vapor deposition particles are vapor-deposited. Alternatively, the films 7 can be provided on at least a part of the surfaces of the vapor deposition preventing plates 3 and the shutter 4 on which surfaces the vapor deposition particles are vapor-deposited.

Further, the films 7 can also be provided only in a region of the vapor deposition preventing plates 3 and the shutter 4 in which region the vapor deposition particles are vapor-deposited in a large amount.

Figure 14:
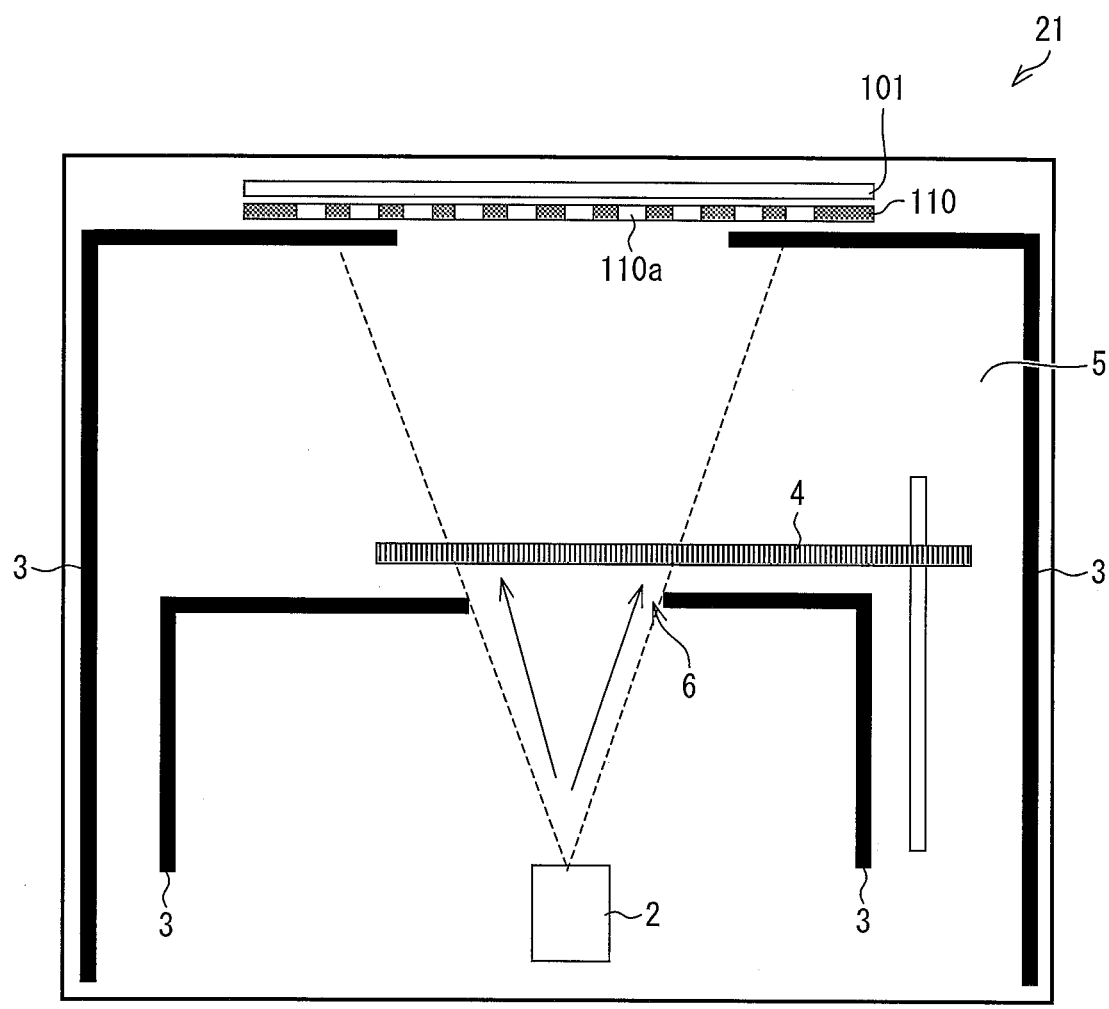
FIG. 14 is a view schematically illustrating a configuration of a conventional vacuum vapor deposition device.
Figure 15:
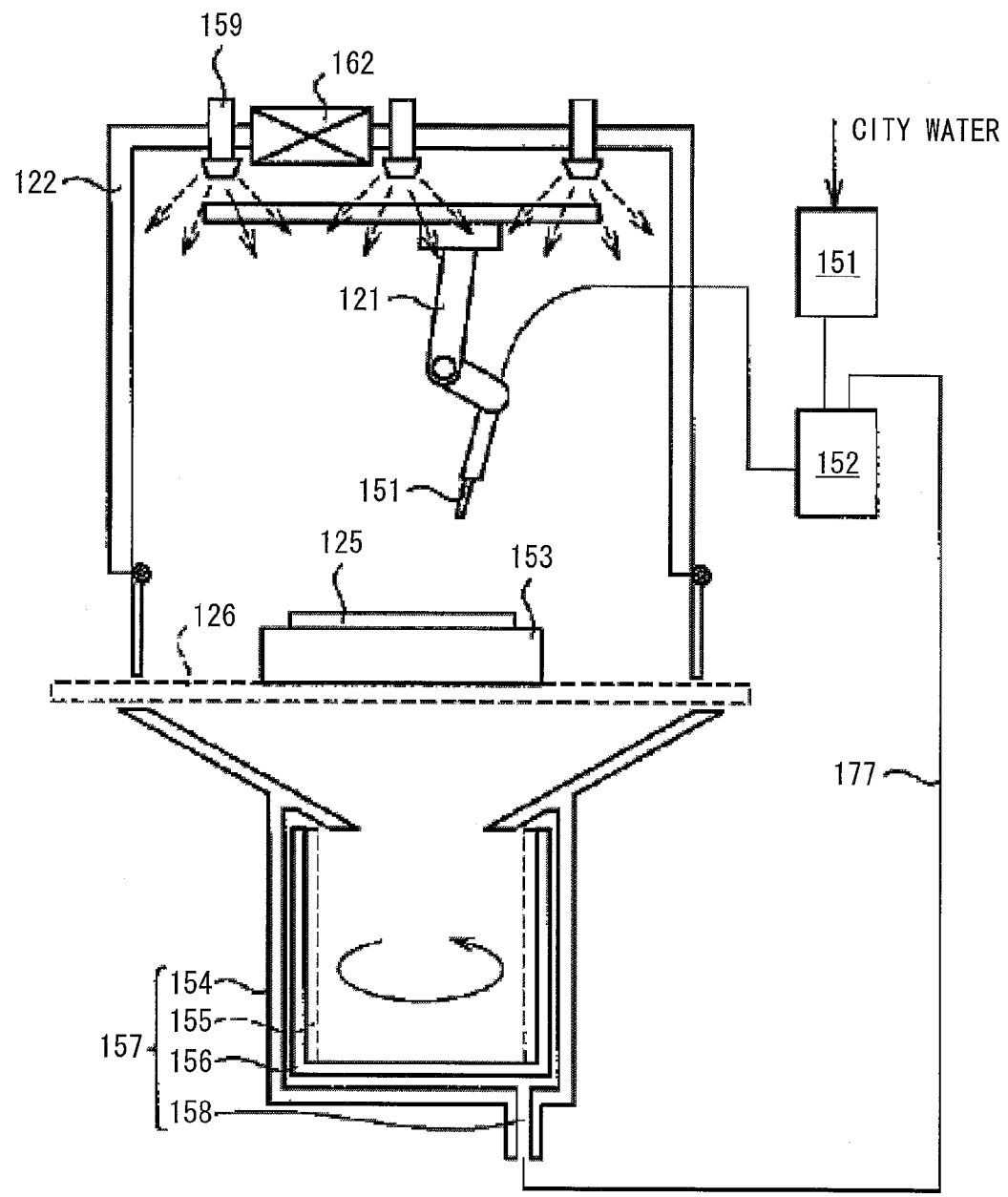
FIG. 15 is a view schematically illustrating a configuration of a water jet device disclosed in Patent Literature 1.

The vacuum vapor deposition device 1 illustrated in FIG. 1 differs from the conventional vacuum vapor deposition device 21 illustrated in FIG. 14 in that the vacuum vapor deposition device 1 includes the films 7 which are provided on the entire surfaces of the vapor deposition preventing plates 3 and of the shutter 4 on which surfaces the vapor deposition particles are vapor-deposited. According to the vacuum vapor deposition device 1, the vapor deposition particles are vapor-deposited on the films 7.

Note that Embodiment 1, the films 7 are adhered, with use of an adhesive, to the surfaces of the vapor deposition preventing plates 3 and of the shutter 4 which are those of the conventional deposition device. However, what is used to adhere the films 7 to the surfaces is not limited to an adhesive, but can be a sticking agent.

Alternatively, the films 7 can be adhered to the surfaces by being pressed against the surfaces with a pin or the like. Further, the films 7 can be formed by spraying or coating the surfaces with a resin and then curing the resin.

Figure 2:
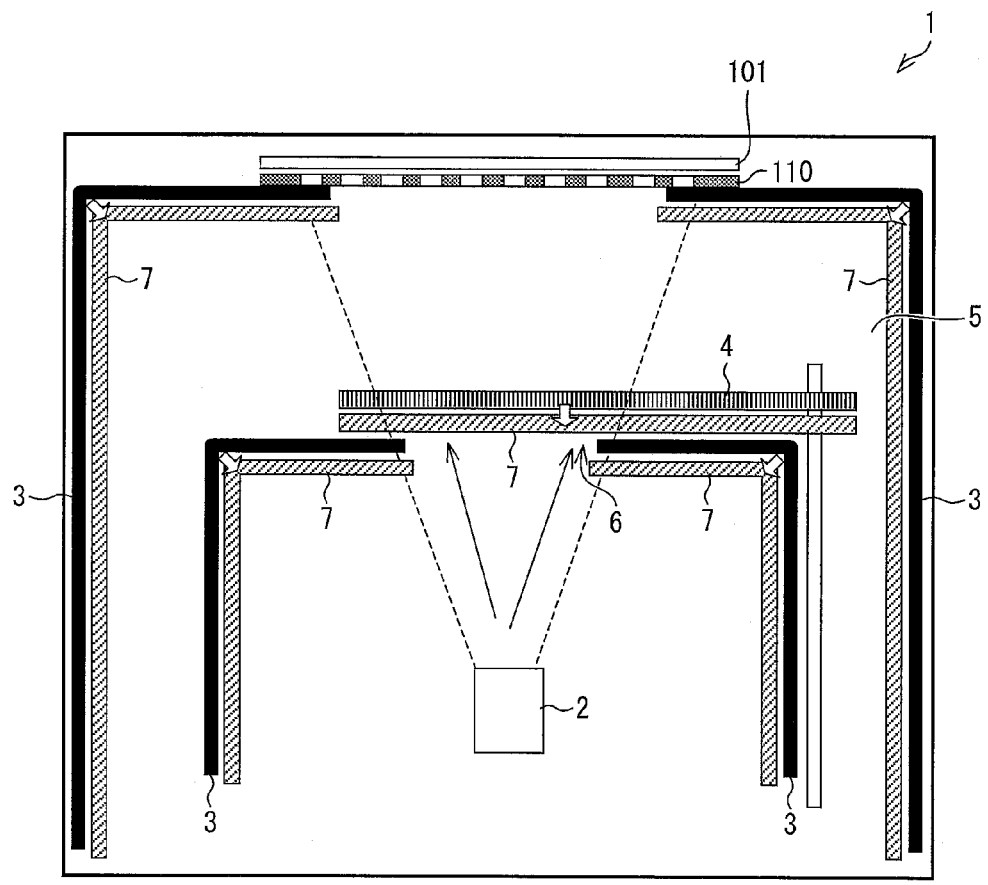
FIG. 2 is a view illustrating a state in which films have been peeled off from vapor deposition preventing plates and a shutter in the vacuum vapor deposition device illustrated in FIG. 1.

FIG. 2 is a view illustrating a state in which the films 7 have been peeled off from the vapor deposition preventing plates and shutter 4 in the vacuum vapor deposition device 1 illustrated in FIG. 1.

As illustrated in FIG. 2, the films 7 can be easily peeled off from the vapor deposition preventing plates 3 and the shutter 4 manually or by mechanical means.

Note that the films 7 are made of a water-soluble material. Embodiment 1 employs, as the films 7, films made of polyvinyl alcohol (PVA). However, the films 7 are not limited to these.

Although the adhesive is also water-soluble in Embodiment 1, an adhesive is not limited to this. Note, however, that, since the adhesive which is not water-soluble remains without being dissolved in water, it is necessary to remove an adhesive component with use of a collection device provided separately from the vacuum vapor deposition device 1.

Meanwhile, a material of which the organic EL layers (e.g., the hole injection layer, the hole transfer layer, the luminescent layer, the electron transfer layer, and the electron injection layer) to be used as the vapor deposition source 2 in the vacuum vapor deposition device 1 and to be vapor-deposited on the films 7 are made is a typically chain or heterocyclic conjugated organic compound. Therefore, in a case where a material of which the organic EL layers are made has no particular functional group (e.g., a carboxyl group or a hydroxy group), the material is water-insoluble.

Hence, in a collection device (described later), the films 7 are dissolved in water, whereas films vapor-deposited on the films 7 are not dissolved in the water. This allows the films 7 and the films vapor-deposited on the films 7 to be easily separated.

Examples of a material of which the organic EL layers usable as the vapor deposition source 2 are made are presented below:

The hole injection layer/hole transfer layer encompass (i) anthracene, azatriphenylene, fluorenone, hydrazone, stilbene, triphenylene, benzine, styryl amine, triphenylamine, porphyrin, triazole, imidazole, oxadiazole, oxazole, polyarylalkane, phenylenediamine, arylamine, or a derivative of any of the above, a monomer, an oligomer, or a polymer of a heterocyclic conjugated system such as a thiophene compound, a polysilane compound, a vinylcarbazole compound, or an aniline compound.

The luminescent layers are each made of a material, such as a low-molecular fluorescent pigment or a metal complex, that has high light emission efficiency. For example, the luminescent layers are each made of a material such as anthracene, naphthalene, indene, phenanthrene, pyrene, naphthacene, triphenylene, perylene, picene, fluoranthene, acephenanthrylene, pentaphene, pentacene, coronene, butadiene, coumarin, acridine, stilbene, a derivative of any of the above and (ii) a tris(8-hydroxyquinolinate) aluminum complex, a bis(benzoquinolinolato) beryllium complex, a tri(dibenzoylmethyl) phenanthroline europium complex, ditolyl vinyl biphenyl, hydroxyphenyl oxazole, or hydroxyphenyl thiazole.

The electron transfer layer and the electron injection layer are each made of a material such as a tris(8-hydroxyquinolinate) aluminum complex, an oxadiazole derivative, a triazole derivative, a phenylquinoxaline derivative, or a silole derivative.

Note that the films vapor-deposited on the films 7 do not necessarily need to be water-insoluble, provided that there is a difference in water solubility between the films 7 and the films vapor-deposited on the films 7. It is preferable that the difference in water solubility be as great as possible.

The films 7 on which the vapor deposition particles are vapor-deposited can thus be easily peeled off from the vapor deposition preventing plates 3 and the shutter 4 and then extracted from the vacuum chamber 5.

The films 7 can also be peeled off from the vapor deposition preventing plates 3 and the shutter 4 after the vapor deposition preventing plates 3 and the shutter 4 are extracted from the vacuum chamber 5. However, a throughput is reduced by an amount of time spent for extraction and replacement of the vapor deposition preventing plates 3 and the shutter 4. Therefore, it is preferable to extract only the films 7 from the vacuum chamber 5.

In a case where new films 7 are adhered again to the vapor deposition preventing plates 3 and the shutter 4 after the films 7 are peeled off, the vacuum vapor deposition device 1 can operate. Therefore, such a method allows the throughput to be higher than a conventional method in which vapor deposition preventing plates 3 and the shutter 4, on each of which the vapor deposition material is adherent, are all replaced with new ones.

Furthermore, there is no need to prepare replacements for the vapor deposition preventing plates 3 and the shutter 4, and therefore reductions in equipment cost and in member storage area can be expected.

Figure 3:
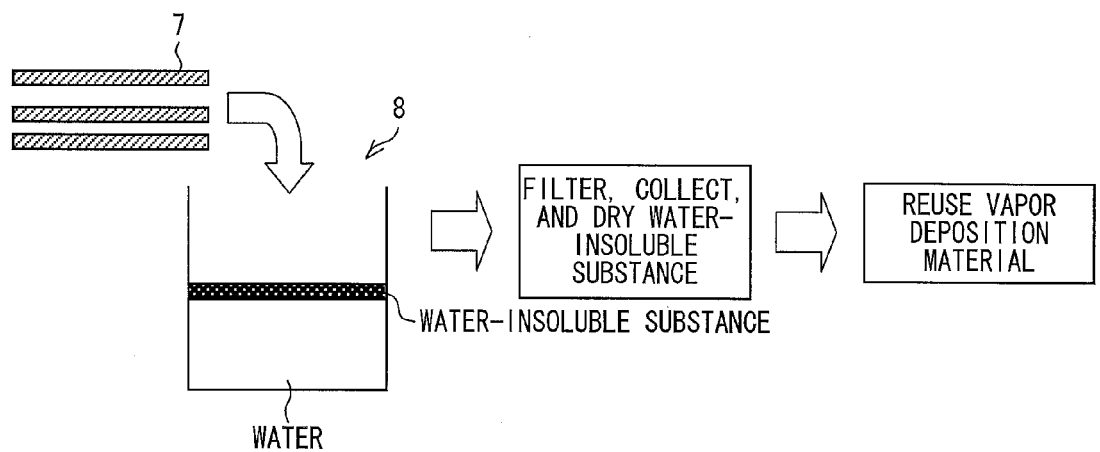
FIG. 3 is a view illustrating (i) a collection device according to Embodiment 1 of the present invention and (ii) a process in which a water-insoluble substance obtained from the collection device is reused as a vapor deposition material.

FIG. 3 is a view illustrating (i) a collection device 8 for separating the films 7 and the films vapor-deposited on the films and (ii) a process in which a water-insoluble substance obtained from the collection device 8 is reused as a vapor deposition material.

As illustrated in FIG. 3, the collection device 8 includes a water tank (separating section). The films 7 on which the films are vapor-deposited are introduced into the water tank.

In a case where only a water-insoluble substance is collected by filtering from an aqueous solution in which the films 7 are dissolved and then the water-insoluble substance is dried, it is possible to obtain a vapor deposition material, so that the deposition material can be reused.

Note that the collection device 8, which includes only the water tank in FIG. 3, further includes a filtering section and a drying section.

Note that according to Embodiment 1, filtering is employed as a method for collecting only a water-insoluble material from an aqueous solution. However, the method is not limited to this.

Note that according to Embodiment 1, the water tank, which is provided in the collection device 8, can be replaced with a tank containing an organic solvent, provided that it is possible to secure a difference in solubility in a predetermined solvent between the films 7 and the films vapor-deposited on the films 7. However, it is more preferable to use water since an organic solvent has more various problems than water (described later).

Note that according to the collection device 8, there is no deterioration in vapor deposition material due to heating since heating is carried out only in a drying step during the process.

Furthermore, unlike a conventional method, adherent films do not need to be scraped off surfaces of a vapor deposition preventing plate, a shutter, and the like, or the adherent films do not need to be directly sprayed with water jet. Therefore, there is no damage to the vapor deposition preventing plate and the shutter, or there is no residue of a vapor deposition material on surfaces of these vapor deposition preventing materials.

Since the films 7 on which vapor-deposited films are formed are flexible, the films 7 can be cut into fine pieces or compressed, so as to be introduced into the water tank.

This allows the films 7 to be processed in a large amount at one time, and allows the collection device 8 to be small in size.

Further, since it is possible to use a single collection device 8 regardless of a size and a shape of a vacuum vapor deposition device, it is possible to reduce an equipment cost.

Meanwhile, it is also possible to collect a vapor deposition material by use of a method in which a vapor deposition preventing plate 3 and a shutter are each made of SUS and the vapor deposition preventing plate and the shutter on each of which the vapor deposition material is adherent are immersed in an organic solvent capable of dissolving a vapor deposition material.

Such a method makes it possible to separate a vapor deposition material from a vapor deposition preventing plate and a shutter by dissolving only the vapor deposition material in an organic solvent, whereas the method has the following problems.

The use of an organic solvent (i) costs higher than the use of water and (ii) necessitates advanced waste liquid treatment and reprocessing facilities.

Furthermore, impurities originally contained in an organic solvent are included in a collected vapor deposition material. Since it is difficult to separate the impurities from the vapor deposition material, it is necessary to highly purify the vapor deposition material by, for example, sublimation and purification. This causes an increase in cost of collecting the vapor deposition material.

Furthermore, a collectable vapor deposition material is limited depending on solubility of a vapor deposition material in an organic solvent.

Furthermore, in a case where films are to be provided to a vapor deposition preventing plate and a shutter as in the case of Embodiment 1, it is necessary to select, for the films, a material that are insoluble in an organic solvent.

Note that the films 7 can be applied not only to a vapor deposition preventing plate and a shutter but also to various structures of a vacuum chamber.

Figure 4:
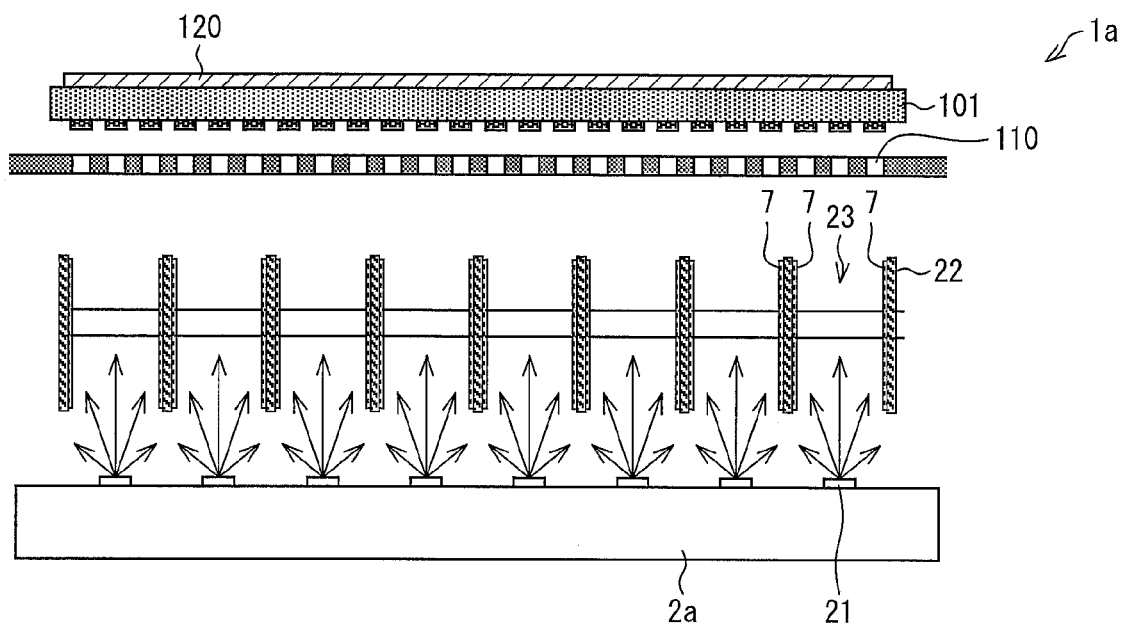
FIG. 4 is a view schematically illustrating a configuration of a vacuum vapor deposition device including control plates each provided with a film, which vacuum vapor deposition device is a modified example of Embodiment 1.

FIG. 4 is a view schematically illustrating a vacuum vapor deposition device 1a including a plurality of control plates 22.

According to the vacuum vapor deposition device 1a, vapor deposition particles having entered inter-control-plate spaces 23 are selectively captured, in accordance with their respective entry angles, by the plurality of control plates 22 (vapor deposition preventing members) which are provided between a vapor deposition source 2a and a vapor deposition mask 110. This causes openings of the vapor deposition mask 110 to receive only vapor deposition particles each having an entry angle that is not more than a predetermined entry angle (see FIG. 4).

This reduces a maximum entry angle at which vapor deposition particles enters a substrate 101. Therefore, it is possible to prevent a blur occurring at an edge of a film formed on the substrate 101 held by a holder 120.

As illustrated in FIG. 4, films 7 can also be provided to the plurality of control plates 22.

Note that the plurality of control plates 22 can be integrated.

Note that according to Embodiment 1, (i) vacuum chambers are prepared in respective steps of the process for producing an organic EL display device (see FIG. 13) and (ii) films 7 are provided to vapor deposition preventing plates 3 and a shutter 4 of each of the respective vacuum chambers used for the steps in which a hole injection layer, a hole transfer layer, a luminescent layer, an electron transfer layer, and an electron injection layer are formed.

[Embodiment 2]

Figure 5:
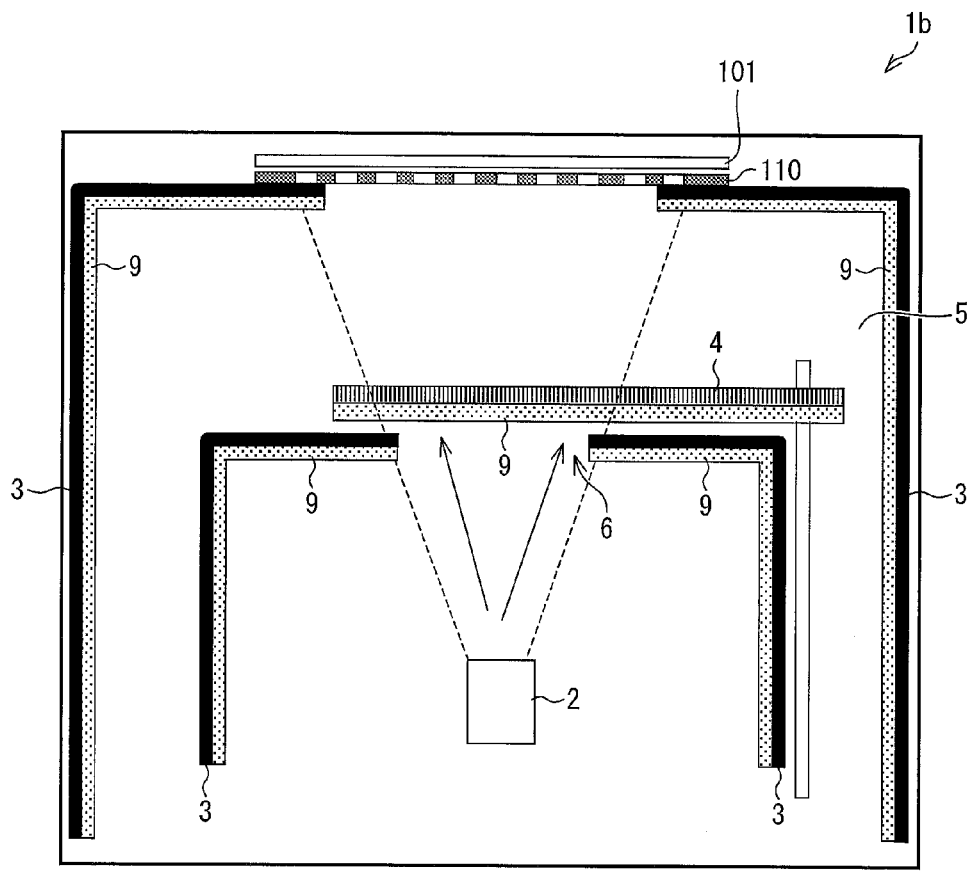
FIG. 5 is a view schematically illustrating a configuration of a vacuum vapor deposition device according to Embodiment 2 of the present invention.
Figure 6:
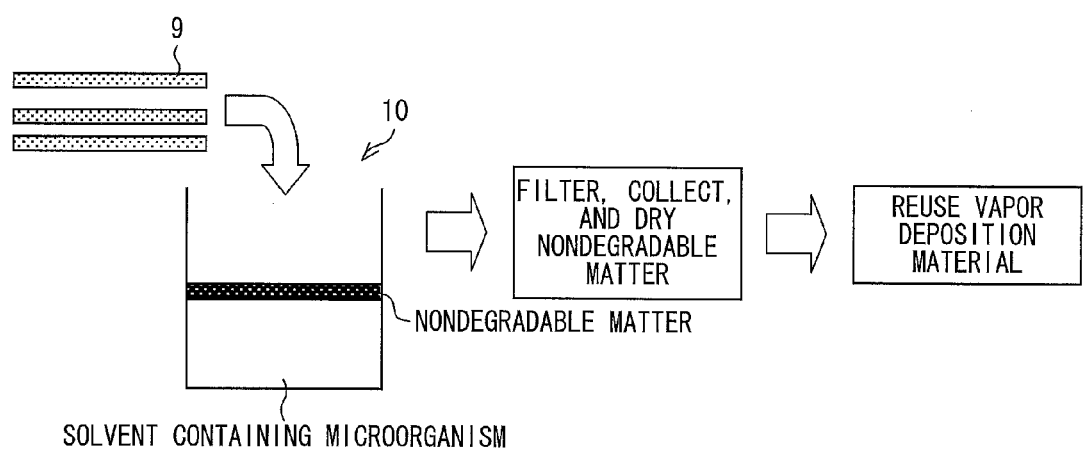
FIG. 6 is a view illustrating (i) a collection device according to Embodiment 2 of the present invention and (ii) a process in which a nondegradable matter obtained from the collection device is reused as a vapor deposition material.

The following description will discuss Embodiment 2 of the present invention with reference to FIGS. 5 and 6. Embodiment 2 differs from Embodiment 1 in that Embodiment 2 uses films 9 made of a biodegradable material. Embodiment 2 is similar to Embodiment 1 except for the above difference. For convenience, members having functions identical to those of the members illustrated in the drawings of Embodiment 1 are given respective identical reference numerals, and a description thereof is not repeated.

FIG. 5 is a view schematically illustrating a configuration of a vacuum vapor deposition device 1b.

As illustrated in FIG. 5, the films 9 made of a biodegradable material are provided on entire surfaces of vapor deposition preventing plates 3 and a shutter 4 on which entire surfaces vapor deposition particles are vapor-deposited, the vapor deposition preventing plates 3 and the shutter 4 each provided in the vacuum vapor deposition device 1b, and the vapor deposition particles are vapor-deposited on the films 9.

The films 9 on which the vapor deposition particles are vapor-deposited can be easily peeled off from the vapor deposition preventing plates 3 and the shutter 4 and then extracted from a vacuum chamber 5.

The films 9 are made of a biodegradable material. Examples of the biodegradable material encompass polylactic acid and polyglycol acid.

Specific examples of the biodegradable material encompass ECOLOJU™ manufactured by Mitsubishi Plastics, Inc. and Hi-selon manufactured by The Nippon Synthetic Chemical Industry Co., Ltd.

The films 9, which are biodegradable, are degraded by microorganisms into water and carbon dioxide.

FIG. 6 is a view illustrating (i) a collection device 10 for separating the films 9 and films vapor-deposited on the films 9 and (ii) a process in which a nondegradable matter obtained from the collection device 10 is reused as a vapor deposition material.

As illustrated in FIG. 6, the collection device 10 includes a microbial degradation tank (separating section). The films 9 on which the films are vapor-deposited are introduced into the microbial degradation tank.

The films 9, which are biodegradable, are degraded by microorganisms. Meanwhile, many of materials for an organic EL layer have benzene rings, which are less biodegradable.

That is, in a case where vapor-deposited films adherent on the films 9 are set to be less biodegradable than the films 9, an undegraded film (nondegradable matter) can remain even if the films 9 are completely degraded.

In a case where the nondegradable matter is collected by separation in accordance with a method such as filtering or washing by water and are then dried, it is possible to obtain a vapor deposition material, so that the vapor deposition material can be reused.

Note that the collection device 10, which includes only the microbial degradation tank in FIG. 6, further includes a filtering section and a drying section.

According to the configuration, the films 9 are made of a biodegradable material. This prevents a harmful by-product from being generated during the step of separating the vapor deposition material from the films 9. Therefore, it is possible to achieve the collection device 10 which is low in environmental load.

According to the collection device 10, it is also possible to use light irradiation in combination, provided that the vapor deposition material does not deteriorate.

In a case where the films 9 are films which can be degraded only by light irradiation, such films can be used instead of biodegradable films. In this case, it is only necessary to replace the microbial degradation tank with a light irradiation process tank. Additionally, it is possible to use water in combination so as to accelerate film degradation by light irradiation.

The films which can be degraded only by light irradiation, i.e., photodegradable plastics (films) can be obtained by use of, for example, a technique disclosed in Japanese Patent No. 2826634 B or Japanese Patent Application Publication, Tokukai, No. 2010-059322 A.

Light that irradiates the films is not particularly limited in wavelength range, provided that the light can degrade the films. For example, the light can be visible light, ultraviolet light (ultraviolet rays), or light containing visible light and ultraviolet light.

Note that according to the collection device 10, there is no deterioration in vapor deposition material due to heating since heating is carried out only in a drying step during the process.

Furthermore, unlike a conventional method, adherent films do not need to be scraped off surfaces of a vapor deposition preventing plate, a shutter, and the like, or the adherent films do not need to be directly sprayed with water jet. Therefore, there is no damage to the vapor deposition preventing plate and the shutter, or there is no residue of a vapor deposition material on surfaces of these vapor deposition preventing materials.

Since the films 9 on which vapor-deposited films are formed are flexible, the films 9 can be cut into fine pieces or compressed, so as to be introduced into the microbial degradation tank.

This allows the films 9 to be processed in a large amount at one time, and allows the collection device 10 to be small in size.

Further, since it is possible to use a single collection device 10 regardless of a size and a shape of a vacuum vapor deposition device, it is possible to reduce an equipment cost.

[Embodiment 3]

Figure 7:
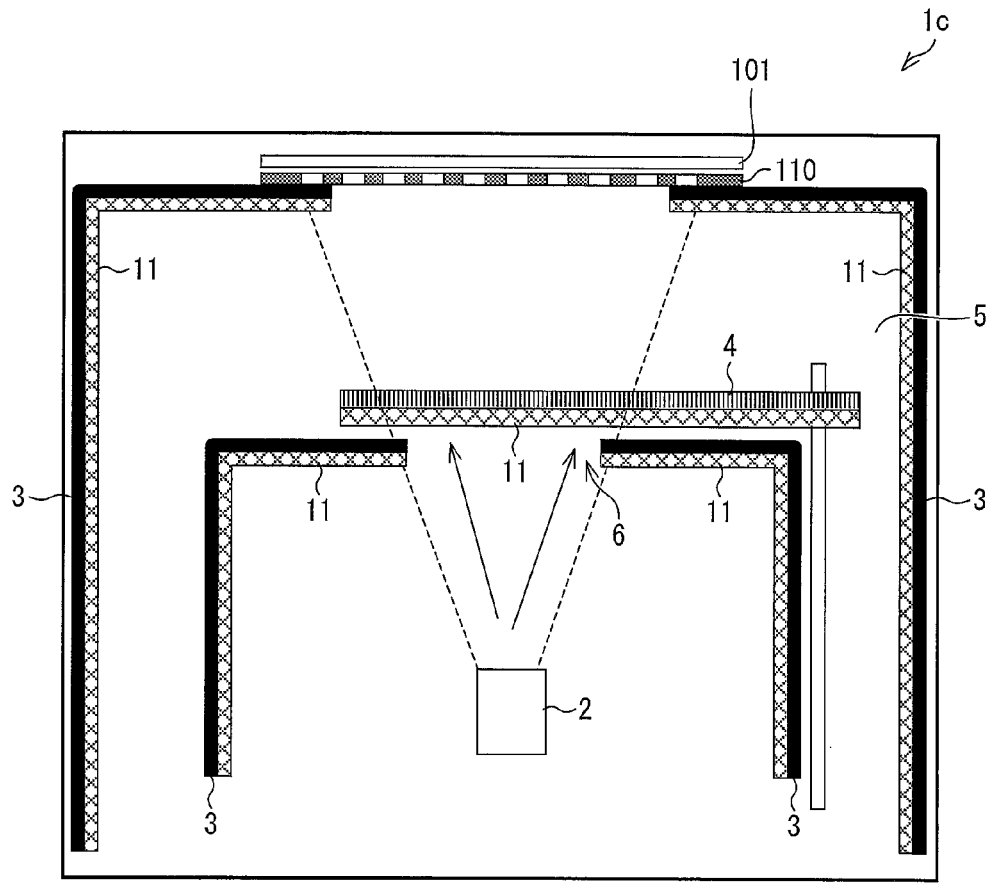
FIG. 7 is a view schematically illustrating a configuration of a vacuum vapor deposition device according to Embodiment 3 of the present invention.
Figure 8:
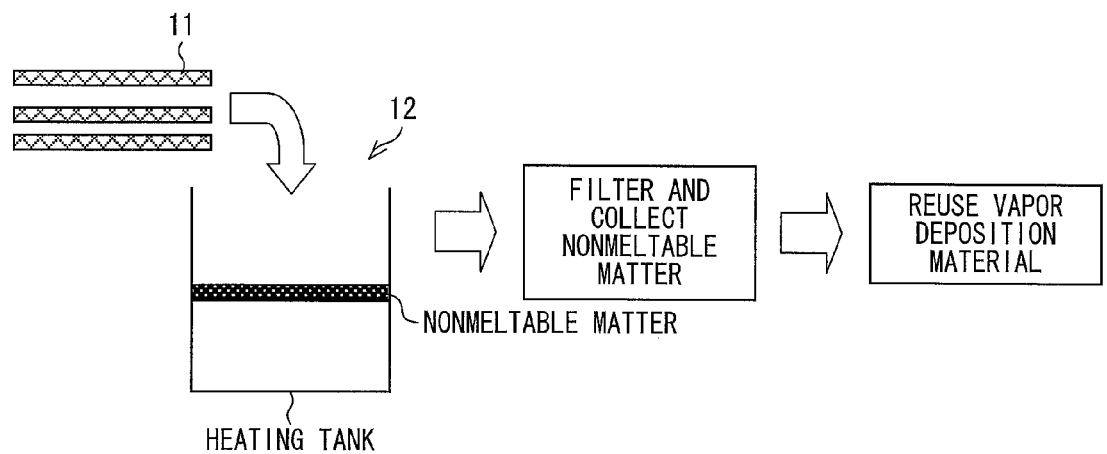
FIG. 8 is a view illustrating (i) a collection device according to Embodiment 3 of the present invention and (ii) a process in which a nondegradable matter obtained from the collection device is reused as a vapor deposition material.

The following description will discuss Embodiment 3 of the present invention with reference to FIGS. 7 and 8. Embodiment 3 differs from Embodiment 1 in that Embodiment 3 uses films 11 made of a low-temperature melting material. Embodiment 3 is similar to Embodiment 1 except for the above difference. For convenience, members having functions identical to those of the members illustrated in the drawings of Embodiment 1 are given respective identical reference numerals, and a description thereof is not repeated.

FIG. 7 is a view schematically illustrating a configuration of a vacuum vapor deposition device 1c.

As illustrated in FIG. 7, the films 11 made of a low-temperature melting material are provided on entire surfaces of vapor deposition preventing plates 3 and a shutter 4 on which entire surfaces vapor deposition particles are vapor-deposited, the vapor deposition preventing plates 3 and the shutter 4 each provided in the vacuum vapor deposition device 1c, and the vapor deposition particles are vapor-deposited on the films 11.

The films 11 on which the vapor deposition particles are vapor-deposited can be easily peeled off from the vapor deposition preventing plates 3 and the shutter 4 and then extracted from a vacuum chamber 5.

The films 11 are made of a low-temperature melting material, examples of which encompass polyethylene and polypropylene. At a normal pressure, polyethylene has a melting point of approximately 120° C., and polypropylene has a melting point of approximately 160° C.

Although the films 11 are made of polypropylene according to Embodiment 3, a material of which the films 11 are made is not limited to this.

FIG. 8 is a view illustrating (i) a collection device 12 for separating the films 11 and films vapor-deposited on the films 11 and (ii) a process in which a nonmeltable matter obtained from the collection device 12 is reused as a vapor deposition material.

As illustrated in FIG. 8, the collection device 12 includes a heating tank (separating section). The films 11 on which the films are vapor-deposited are introduced into the heating tank.

Since an inside of the heating tank is maintained in an inert gas or a vacuum atmosphere and the films 11 are meltable at a low temperature, the films 11 are liquefied by being heated to a temperature which is not less than its melting point.

Meanwhile, since a material of which organic EL layers are made by a vacuum vapor deposition method is typically a low-molecular one, and has a high melting point or sublimation point. This causes the material to be supernatant, floating, or precipitated without being liquefied. The melting point or sublimation point of the material of which the organic EL layers are made is, for example, approximately 200° C. to 350° C.

Since the inside of the heating tank is in an inert gas atmosphere or a vacuum, a nonmeltable matter does not easily deteriorate by being heated.

The nonmeltable matter can be collected by separation by filtering or the like. Melting by use of the heating tank and the collection by separation by filtering can be carried out a plurality of times if necessary.

This allows a further increase in purity of a vapor deposition material to be obtained.

The vapor deposition material can thus be collected and reused.

Note that the collection device 12, which includes only the heating tank in FIG. 8, further includes a filtering section.

Note that, in a case where films have a lower melting point than a melting point or a sublimation point of vapor-deposited films vapor-deposited on the films 11, it is possible to employ such a method as described above.

Note also that the method can be employed in a case where films having a sublimation point instead of a melting point are used and the films have a lower sublimation point than a melting point or a sublimation point of vapor-deposited films vapor-deposited on the films. Note, however, that it is necessary in this case to provide, instead of carrying out a filtering process, the heating tank with an outlet via which a film material sublimated in the heating tank is discharged.

According to the collection device 12, a molten material of which the films 11 are made can be reused by being made into films again. Therefore, it is possible to reuse both the films 11 and a vapor deposition material vapor-deposited on the films 11, and to allow a further reduction in waste to be produced during a vapor deposition step carried out by the organic EL display device.

Since the films 11 on which vapor-deposited films are formed are flexible, the films 11 can be cut into fine pieces or compressed, so as to be introduced into the heating tank.

This allows the films 11 to be processed in a large amount at one time, and allows the collection device 12 to be small in size.

Further, since it is possible to use a single collection device 12 regardless of a size and a shape of a vacuum vapor deposition device, it is possible to reduce an equipment cost.

[Embodiment 4]

Figure 9:
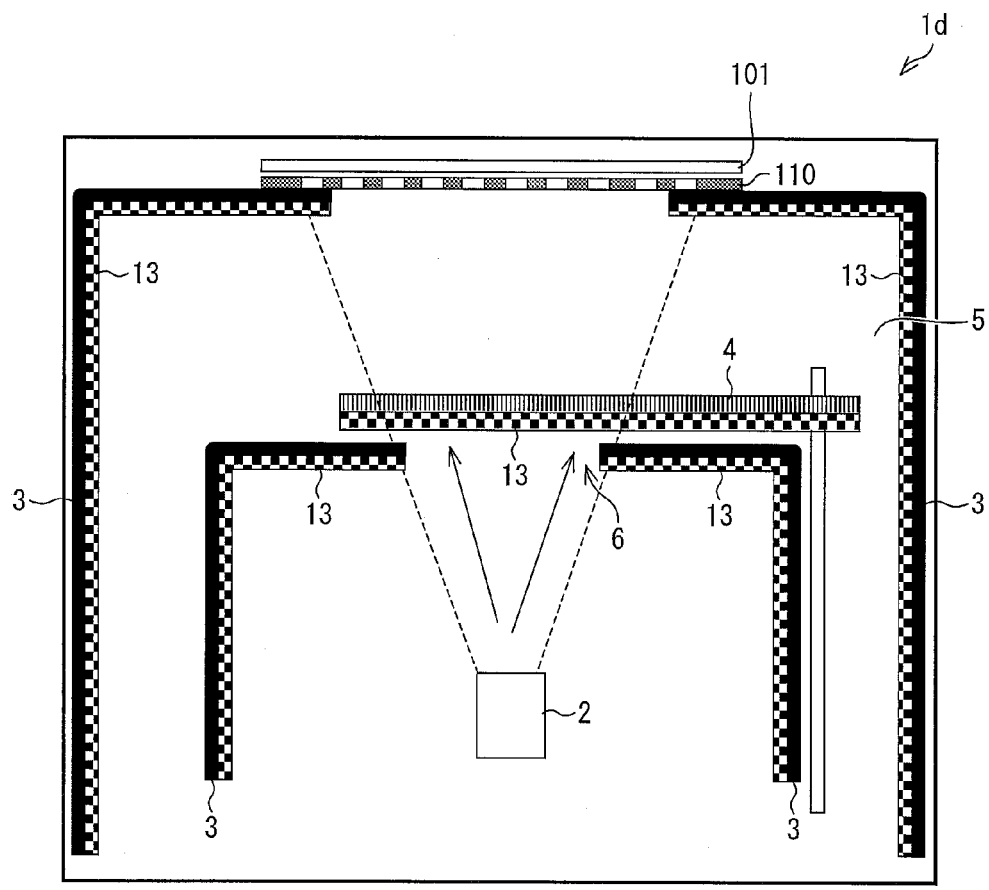
FIG. 9 is a view schematically illustrating a configuration of a vacuum vapor deposition device according to Embodiment 4 of the present invention.
Figure 10:
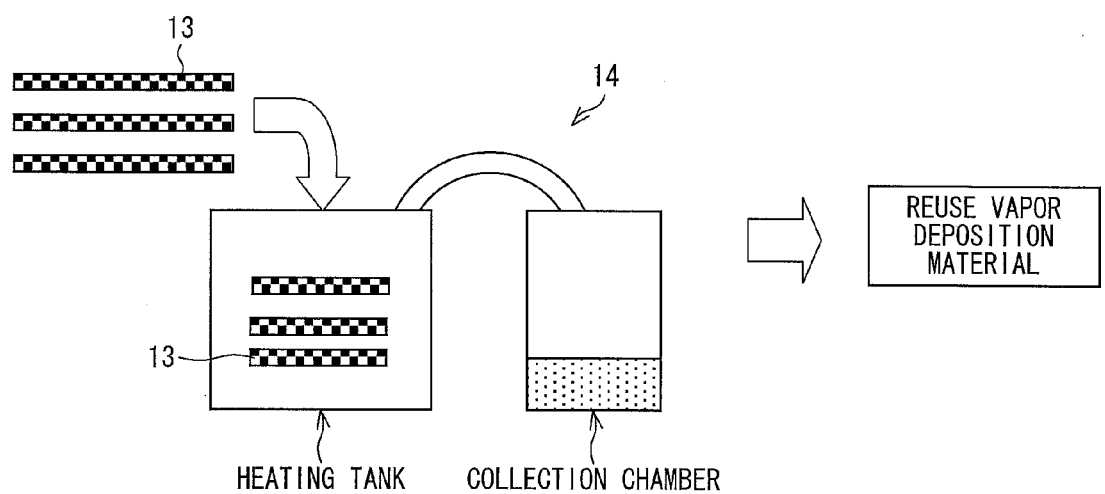
FIG. 10 is a view illustrating (i) a collection device according to Embodiment 4 of the present invention and (ii) a process in which a vapor deposition material obtained from the collection device is reused.

The following description will discuss Embodiment 4 of the present invention with reference to FIGS. 9 and 10. Embodiment 4 differs from Embodiment 1 in that Embodiment 4 uses films 13 made of a heat-resistant material. Embodiment 4 is similar to Embodiment 1 except for the above difference. For convenience, members having functions identical to those of the members illustrated in the drawings of Embodiment 1 are given respective identical reference numerals, and a description thereof is not repeated.

FIG. 9 is a view schematically illustrating a configuration of a vacuum vapor deposition device 1d.

As illustrated in FIG. 9, the films 13 made of a heat-resistant material are provided on entire surfaces of vapor deposition preventing plates 3 and a shutter 4 on which entire surfaces vapor deposition particles are vapor-deposited, the vapor deposition preventing plates 3 and the shutter 4 each provided in the vacuum vapor deposition device 1d, and the vapor deposition particles are vapor-deposited on the films 13.

The films 13 on which the vapor deposition particles are vapor-deposited can be easily peeled off from the vapor deposition preventing plates 3 and the shutter 4 and then extracted from a vacuum chamber 5.

The films 13 are heat-resistant films. According to Embodiment 4, the films 13 are made of aluminum foil. However, a material of which the films 13 are made is not limited to this.

FIG. 10 is a view illustrating (i) a collection device 14 for separating the films 13 and films vapor-deposited on the films 13 and (ii) a process in which a vapor deposition material obtained from the collection device 14 is reused.

As illustrated in FIG. 10, the collection device 14 includes a heating tank (sublimation and purification tank). The films 13 on which the films are vapor-deposited are introduced into the heating tank.

The heating tank, an inside of which is maintained in a vacuum atmosphere, is heated to sublimate the films vapor-deposited on the films 13.

The films 13, which are heat-resistant, are not denatured even by being heated.

A sublimate is cooled in the collection chamber so as to be re-solidified. Such a process makes it possible to collect and reuse a vapor deposition material.

Note that such a sublimation and purification process can be repeated a plurality of times by reintroducing, into the heating tank (sublimation and purification tank), the vapor deposition material collected in the collection chamber (collecting section).

Further, it is possible to reintroduce the vapor deposition material collected in the collection chamber into the heating tank (sublimation and purification tank) while mixing the vapor deposition material with the films 13 peeled off from the vapor deposition preventing plates 3 and the shutter 4.

In a case where the sublimation and purification process is repeated, it is possible to further increase purity of the vapor deposition material.

Note that it is possible to employ, as a material of which the films 13 that are heat-resistant is made, a material which is resistant to heat at a temperature higher than a sublimation temperature of the films vapor-deposited on the films 13.

Metal materials, many of which are generally not denatured at a sublimation temperature of a material of which organic EL layers are made, can be suitably employed as film materials.

After the vapor deposition material vapor-deposited on the films 13 is peeled off by sublimation, the films 13 can be reused as they are.

Therefore, it is possible to reuse both the films 13 and the vapor deposition material vapor-deposited on the films 13, and to allow a further reduction in waste to be produced during a vapor deposition step carried out by the organic EL display device.

Since the films 13 on which vapor-deposited films are formed are flexible, the films 13 can be cut into fine pieces or compressed, so as to be introduced into the heating tank.

This allows the films 13 to be processed in a large amount at one time, and allows the collection device 14 to be small in size.

Further, since it is possible to use a single collection device 14 regardless of a size and a shape of a vacuum vapor deposition device, it is possible to reduce an equipment cost.

The vapor deposition device of the present invention is preferably configured such that: the material of which the film is made differs in solubility in water from the material of which the vapor-deposited film that is formed on the film is made; and the material of which the film is made has greater solubility in water than the material of which the vapor-deposited film that is formed on the film is made.

With the configuration, it is possible to separate, with use of water, the film and the vapor-deposited film that is formed on the film.

The vapor deposition device of the present invention is preferably configured such that: the film is water-soluble; and the vapor-deposited film that is formed on the film is water-insoluble.

The vapor deposition device of the present invention is preferably configured such that the film is made of polyvinyl alcohol.

With the configuration, it is possible to efficiently separate, with use of water, the film and the vapor-deposited film that is formed on the film.

The vapor deposition device of the present invention is preferably configured such that: the material of which the film is made differs in microbial biodegradability from the material of which the vapor-deposited film that is formed on the film is made; and the material of which the film is made has greater microbial biodegradability than the material of which the vapor-deposited film that is formed on the film is made.

The vapor deposition device of the present invention is preferably configured such that the film is made of polylactic acid or polyglycol acid.

With the configuration, it is possible to prevent a harmful by-product from being generated during the step of separating the film and the vapor-deposited film that is formed on the film, so that an environmental load can be reduced.

The vapor deposition device of the present invention is preferably configured such that: the material of which the film is made differs in photodegradability from the material of which the vapor-deposited film that is formed on the film is made; and the material of which the film is made has greater photodegradability than the material of which the vapor-deposited film that is formed on the film is made.

With the configuration, it is possible to separate, with use of light, the film and the vapor-deposited film that is formed on the film.

The vapor deposition device of the present invention is preferably configured such that: the material of which the film is made differs in melting point or sublimation point from the material of which the vapor-deposited film that is formed on the film is made; and the material of which the film is made has a lower melting point or sublimation point than the material of which the vapor-deposited film that is formed on the film is made.

The vapor deposition device of the present invention is preferably configured such that the film is made of polyethylene or polypropylene.

With the configuration, a molten film can be reused by being made into a film again. Therefore, it is possible to reuse both the film and the vapor-deposited film that is formed on the film, and to allow a further reduction in waste.

The vapor deposition device of the present invention is preferably configured such that: the material of which the film is made differs in sublimation point from the material of which the vapor-deposited film that is formed on the film is made; and the material of which the film is made has a higher sublimation point than the material of which the vapor-deposited film that is formed on the film is made.

The vapor deposition device of the present invention is preferably configured such that the film is made of aluminum foil.

With the configuration, after the vapor-deposited film that is formed on the film is peeled off by sublimation, the film can be reused as it is.

Therefore, it is possible to reuse both the film and the vapor-deposited film that is formed on the film, and to allow a further reduction in waste.

The vapor deposition device of the present invention is preferably configured such that the vapor deposition preventing member includes a vapor deposition preventing plate for preventing the vapor deposition chamber from being contaminated with the vapor deposition particles.

The vapor deposition device of the present invention is preferably configured such that the vapor deposition preventing member includes a shutter for preventing the vapor deposition particles released from the vapor deposition source from being vapor-deposited on the substrate during the second period.

The vapor deposition device of the present invention is preferably configured such that: the vapor deposition preventing member includes (i) a plurality of control plates which are provided between (a) an opening via which the vapor deposition particles are released from the vapor deposition source and (b) the substrate, and which are provided in a direction perpendicular to a normal direction of the substrate so that the opening is provided between the plurality of control plates, or (ii) the plurality of control plates which are integrated.

According to the configuration, the vapor deposition preventing member which is provided with the film is a vapor deposition preventing plate, a shutter, a control plate, and/or the like on each of which the vapor deposition particles are vapor-deposited in a large amount. This makes it possible to efficiently collect a vapor deposition material.

The collection device of the present invention is preferably configured such that: the film is made of a material differing in solubility in water from a material of which the vapor-deposited film that is formed on the film is made; and the collection device includes a water tank as the separating section.

With the configuration, it is possible to efficiently separate, with use of water, the film and the vapor-deposited film that is formed on the film.

Since the film on which the vapor-deposited film is formed is flexible, the film can be cut into fine pieces or compressed, so as to be introduced into the water tank. This allows the film to be processed in a large amount at one time, and allows the collection device to be small in size.

Further, since it is possible to use a single collection device regardless of a size or a shape of the vapor deposition device, it is possible to reduce an equipment cost.

The collection device of the present invention is preferably configured such that: the film is made of a material differing in microbial biodegradability from a material of which the vapor-deposited film that is formed on the film is made; and the collection device includes a microorganism-containing microbial degradation tank as the separating section.

With the configuration, it is possible to prevent a harmful by-product from being generated during the step of separating the film and the vapor-deposited film that is formed on the film, so that an environmental load can be reduced.

Since the film on which the vapor-deposited film is formed is flexible, the film can be cut into fine pieces or compressed, so as to be introduced into the water tank containing microorganisms. This allows the film to be processed in a large amount at one time, and allows the collection device to be small in size.

Further, since it is possible to use a single collection device regardless of a size or a shape of the vapor deposition device, it is possible to reduce an equipment cost.

The collection device of the present invention is preferably configured such that: the film is made of a material differing in melting point or sublimation point from a material of which the vapor-deposited film that is formed on the film is made; and the collection device includes a heating tank as the separating section.

With the configuration, a molten film can be reused by being made into a film again. Therefore, it is possible to reuse both the film and the vapor-deposited film that is formed on the film, and to allow a further reduction in waste.

With the configuration, after the vapor-deposited film that is formed on the film is peeled off by sublimation, the film can be reused as it is. Therefore, it is possible to reuse both the film and the vapor-deposited film that is formed on the film, and to allow a further reduction in waste.

Since the film on which the vapor-deposited film is formed is flexible, the film can be cut into fine pieces or compressed, so as to be introduced into the heating tank. This allows the film to be processed in a large amount at one time, and allows the collection device to be small in size.

Further, since it is possible to use a single collection device regardless of a size or a shape of the vapor deposition device, it is possible to reduce an equipment cost.

The collection device of the present invention is preferably configured such that, in a case where the film has a lower sublimation point than the vapor-deposited film that is formed on the film, the heating tank is provided with an outlet.

The collection device of the present invention is preferably configured such that, in a case where the film has a higher sublimation point than the vapor-deposited film that is formed on the film, the heating tank is connected to a collecting section for collecting a sublimate from the vapor-deposited film that is formed on the film.

With the configuration, after the vapor-deposited film that is formed on the film is peeled off by sublimation, the film can be reused as it is.

Therefore, it is possible to reuse both the film and the vapor-deposited film that is formed on the film, and to allow a further reduction in waste.

The collection device of the present invention can be configured such that: the film is made of a material having greater photodegradability than a material of which the vapor-deposited film that is formed on the film is made; and the collection device includes a light irradiation process tank as the separating section.

With the configuration, it is possible to use light to during the step of separating the film and the vapor-deposited film that is formed on the film.

The collection device of the present invention can be configured such that the microorganism-containing biodegradation tank includes a light irradiating section.

With the configuration, it is possible to use light irradiation in combination, provided that the vapor deposition material does not deteriorate. This allows the vapor deposition material to be collected in a shorter time.

The present invention is not limited to the description of the embodiments above, but may be altered by a skilled person within the scope of the claims. An embodiment based on a proper combination of technical means disclosed in different embodiments is encompassed in the technical scope of the present invention.

INDUSTRIAL APPLICABILITY

The present invention is applicable to a vapor deposition device and to a collection device for collecting vapor deposition materials.

REFERENCE SIGNS LIST 1, 1a, 1b, 1c, 1d Vacuum vapor deposition device (vapor deposition device)
2 Vapor deposition source
3 Vapor deposition preventing plate (vapor deposition preventing member)
4 Shutter (vapor deposition preventing member)
5 Vacuum chamber (vapor deposition chamber)
7, 9, 11, 13 Film
8, 10, 12, 14 Collection device
22 Control plate (vapor deposition preventing member)
101 Substrate
110 Shadow mask

The invention claimed is:

1. A method of producing an organic EL element while collecting a vapor deposition material that is vapor-deposited on a vapor deposition device including a vapor deposition source, a vapor deposition mask, and a substrate,
said vapor deposition device including, between the vapor deposition source and the vapor deposition mask, a plurality vapor deposition preventing members each one of which is (i) removable from the vapor deposition device and (ii) prevents a component in a vapor deposition chamber of the vapor deposition device from being contaminated with vapor deposition particles,
said method comprising the steps of:
(i) providing, on a surface of each vapor deposition preventing member that is perpendicular to the substrate, a film which can be peeled off;
(ii) releasing vapor deposition particles from a vapor deposition source of the vapor deposition device,
(iii) peeling off, from at least one vapor deposition preventing member, the film on which the vapor deposition particles having been released from the vapor deposition source are vapor-deposited; and
(iv) separating, by use of a separating section, the film from a vapor-deposited film having been vapor-deposited on the film, and then collecting the vapor-deposited film,
the film being made of:
polylactic acid or polyglycol acid, any of which has greater microbial biodegradability than does the vapor-deposited film;
polyethylene or polypropylene, any of which has a lower melting point or sublimation point than does the vapor-deposited film; or
a material having greater photodegradability than does the vapor-deposited film.

2. The method as set forth in claim 1, further comprising the step of:
(v) reusing, as a vapor deposition source of the vapor deposition device, the vapor-deposited film collected in the step (iv).

3. The method as set forth in claim 1, wherein, in a case where the film is made of polylactic acid or polyglycol acid, the step (iv) is carried out such that (i) the film is separated from the vapor-deposited film by use of a microorganism-containing microbial degradation tank as the separating section and then (ii) the vapor-deposited film is collected.

4. The method as set forth in claim 3, wherein the microorganism-containing microbial degradation tank used in the step (iv) includes a light irradiating section.

5. The method as set forth in claim 1, wherein, in a case where the film is made of a material having greater photodegradability than does the vapor-deposited film, the step (iv) is carried out such that (i) the film is separated from the vapor-deposited film by use of a light irradiation process tank as the separating section and then (ii) the vapor-deposited film is collected.

6. The method as set forth in claim 1, wherein, in a case where the film is made of polyethylene or polypropylene, the step (iv) is carried out such that (i) the film is separated from the vapor-deposited film by use of a heating tank as the separating section and then (ii) the vapor-deposited film is collected.

7. The method as set forth in claim 1, wherein,
the vapor deposition preventing members comprise (i) a plurality of control plates which are provided in a direction perpendicular to a normal direction of the substrate so that an opening via which the vapor deposition particles are released from the vapor deposition source is provided between the plurality of control plates or (ii) a plurality of control plates which are integrated; and
vapor deposition particles having entered a space are selectively captured, in accordance with their respective entry angles, by the plurality of control plates.

8. A method of collecting a vapor-deposited film by use of a collection device,
said collection device comprising:
a film on which a vapor-deposited film is formed and which is provided in a vapor deposition device including a vapor deposition source, a vapor deposition mask, and a substrate, the film on which the vapor-deposited film is formed being flexible; and
a separating section for separating the vapor-deposited film from the film on which the vapor-deposited film is formed,
the vapor deposition device including: a vapor deposition chamber in which:

vapor deposition particles are vapor-deposited on a substrate when released from a vapor deposition source in a first direction during a first period, the vapor deposition particles are vapor-deposited on a vapor deposition preventing member when released from the vapor deposition source in a second direction, which is different from the first direction, during the first period, the vapor deposition preventing member being removable from the vapor deposition device and preventing components in the vapor deposition chamber from being contaminated with the vapor deposition particles, the vapor deposition preventing member is (i) a plurality of control plates which are provided between the vapor deposition source and the vapor deposition mask so as to be removable from the vapor deposition device, and which are provided in a direction perpendicular to a normal direction of the substrate so that an opening via which the vapor deposition particles are released from the vapor deposition source is provided between the plurality of control plates or (ii) the plurality of control plates which are integrated, and the film is provided on both sides of part of at least one of the plurality of control plates on which the vapor deposition particles are vapor-deposited, the film being provided so as to be peeled off from the at least one of the plurality of control plates, the film being configured to collect and reuse the vapor deposition particles, the film being made of (i) a material differing in microbial biodegradability from a material of which the vapor-deposited film that is formed on the film is made or (ii) a material having greater photodegradability than a material of which the vapor-deposited film that is formed on the film is made, the separating section being a microorganism-containing microbial degradation tank in a case where the film is made of the material differing in microbial biodegradability from the material of which the vapor-deposited film that is formed the film is made, and the separating section being a light irradiation process tank in a case where the film is made of the material having greater photodegradability than the material of which the vapor-deposited film that is formed on the film is made;

said method comprising a step of collecting, from the film provided in the collection device, a vapor-deposited film that is formed on the film, said step including the steps of:

(i) providing the film on both sides of part of at least one of the plurality of control plates so as to be peeled off;

(ii) releasing vapor deposition particles from the vapor deposition source of the vapor deposition device, (iii) peeling off, from the at least one of the plurality of control plates, the film on which the vapor deposition particles having been released from the vapor deposition source are vapor-deposited; and (iv) separating, by use of the separating section, the film from the vapor-deposited film having been formed on the film, and then collecting the vapor-deposited film.

9. A method of producing an organic EL element by use of a collection device, said collection device comprising:

a film on which a vapor-deposited film is formed and which is provided in a vapor deposition device including a vapor deposition source, a vapor deposition mask, and a substrate, the film on which the vapor-deposited film is formed being flexible; and a separating section for separating the vapor-deposited film from the film on which the vapor-deposited film is formed, the vapor deposition device including: a vapor deposition chamber in which:

vapor deposition particles are vapor-deposited on the substrate when released from a vapor deposition source in a first direction during a first period, the vapor deposition particles are vapor-deposited on a vapor deposition preventing member when released from the vapor deposition source in a second direction, which is different from the first direction, during the first period, the vapor deposition preventing member being removable from the vapor deposition device and preventing components in the vapor deposition chamber from being contaminated with the vapor deposition particles, the vapor deposition preventing member is (i) a plurality of control plates which are provided between the vapor deposition source and the vapor deposition mask so as to be removable from the vapor deposition device, and which are provided in a direction perpendicular to a normal direction of the substrate so that an opening via which the vapor deposition particles are released from the vapor deposition source is provided between the plurality of control plates or (ii) the plurality of control plates which are integrated, and the film is provided on both sides of part of at least one of the plurality of control plates on which the vapor deposition particles are vapor-deposited, the film being provided so as to be peeled off from the at least one of the plurality of control plates, the film being configured to collect and reuse the vapor deposition particles, the film being made of (i) a material differing in microbial biodegradability from a material of which the vapor-deposited film that is formed on the film is made or (ii) a material having greater photodegradability than a material of which the vapor-deposited film that is formed on the film is made, the separating section being a microorganism-containing microbial degradation tank in a case where the film is made of the material differing in microbial biodegradability from the material of which the vapor-deposited film that is formed the film is made, and the separating section being a light irradiation process tank in a case where the film is made of the material having greater photodegradability than the material of which the vapor-deposited film that is formed on the film is made;

said method comprising a step of forming the flexible film which is provided in the collection device and on which a vapor-deposited film is formed, said step including the steps of:

(i) providing the film on both sides of part of at least one of the plurality of control plates so as to be peeled off; and (ii) releasing vapor deposition particles from the vapor deposition source of the vapor deposition device so as to simultaneously (a) form, via the vapor deposition mask having openings in respective desired positions thereof, the vapor-deposited film on the substrate and (b) vapor-deposit vapor deposition particles on the film.

* * * * *